(12) United States Patent
Osborne et al.

(10) Patent No.: US 9,096,952 B2
(45) Date of Patent: Aug. 4, 2015

(54) METHODS AND COMPOSITIONS FOR POLYNUCLEOTIDE LIBRARY PRODUCTION, IMMORTALIZATION AND REGION OF INTEREST EXTRACTION

(75) Inventors: Robert Osborne, Walden (GB); Andrew Slatter, London (GB)

(73) Assignee: Population Genetics Technologies LTD., Cambridge (GB)

( * ) Notice: Subject to any disclaimer, the term of this patent is extended or adjusted under 35 U.S.C. 154(b) by 844 days.

(21) Appl. No.: 13/164,153

(22) Filed: Jun. 20, 2011

(65) Prior Publication Data
US 2011/0319299 A1    Dec. 29, 2011

Related U.S. Application Data

(60) Provisional application No. 61/358,345, filed on Jun. 24, 2010.

(51) Int. Cl.
*C40B 20/06*    (2006.01)
*C40B 50/06*    (2006.01)
*C12N 15/10*    (2006.01)

(52) U.S. Cl.
CPC ............ *C40B 50/06* (2013.01); *C12N 15/1093* (2013.01)

(58) Field of Classification Search
CPC ..................................................... C40B 50/06
USPC ........................................................... 506/26
See application file for complete search history.

(56) References Cited

U.S. PATENT DOCUMENTS

| | | | |
|---|---|---|---|
| 4,994,370 A | 2/1991 | Silver et al. | |
| 6,054,300 A | 4/2000 | McKendree | |
| 6,312,913 B1 | 11/2001 | Wang et al. | |
| 6,372,434 B1 * | 4/2002 | Weissman et al. | ........... 435/6.13 |
| 7,790,388 B2 | 9/2010 | Landegren et al. | |

(Continued)

FOREIGN PATENT DOCUMENTS

| | | | |
|---|---|---|---|
| WO | WO 2008/033442 A2 | 3/2008 | |
| WO | WO 2006/014869 A1 | 2/2009 | |

OTHER PUBLICATIONS

Poldoros et al. (BioTechniques, 2006, vol. 41, pp. 35-42, "Rolling circle amplification-RACE: A method for simultaneous isolation of 5' and 3' cDNA ends from amplified cDNA templates").*

(Continued)

*Primary Examiner* — Christopher M Gross
*Assistant Examiner* — Richard L Manteuffel
(74) *Attorney, Agent, or Firm* — James S. Keddie; Bozicevic, Field & Francis, LLP

(57) ABSTRACT

Aspects of the present invention are drawn to methods and compositions for the genetic analysis of regions of interest (ROI) from one or more starting polynucleotide sample(s). In certain aspects, adapter tagged polynucleotide fragments from a plurality of initial polynucleotide samples are pooled, circularized and amplified to produce an immortalized library. Multiple ROI's from this immortalized library are amplified (e.g., in independent iPCR reactions) to generate amplicons, and, in some embodiments, pooled to form a pooled ROI amplicon sample. In certain embodiments, the amplicons for each ROI amplicon in the pooled ROI amplicon sample are present at known molar or mass ratios. The pooled ROI amplicon sample can be analyzed/processed as desired, e.g., sequenced using next generation sequencing technology.

18 Claims, 21 Drawing Sheets

(56) References Cited

U.S. PATENT DOCUMENTS

| | | | |
|---|---|---|---|
| 7,883,849 B1 | 2/2011 | Dahl | |
| 8,298,767 B2* | 10/2012 | Brenner et al. | 435/6.1 |
| 2003/0165979 A1* | 9/2003 | Chui et al. | 435/6 |
| 2008/0096255 A1 | 4/2008 | Harbers et al. | |
| 2008/0131899 A1 | 6/2008 | Landegren et al. | |

OTHER PUBLICATIONS

Dean et al. (Genome Research, 2001, vol. 11, pp. 1095-1099, "Rapid amplification of plasmid and phage DNA using Phi29 DNA polymerase and multiply-primed rolling circle amplification").*

Casbon, et al. A method for counting PCR template molecules with application to next-generation sequencing. Nucleic Acids Res. Jul. 2011;39(12):e81.

Dahl, et al. Multiplex amplification enabled by selective circularization of large sets of genomic DNA fragments. Nucleic Acids Res. Apr. 28, 2005,33(8):e71.

Fredriksson, et al. Multiplex amplification of all coding sequences within 10 cancer genes by Gene-Collector. Nucleic Acids Res. 2007;35(7):e47.

Fu, et al. Counting individual DNA molecules by the stochastic attachment of diverse labels. Proc Natl Acad Sci U S A. May 31, 2011;108(22):9026-31.

Gadkar, et al. A novel method to perform genomic walks using a combination of single strand DNA circularization and rolling circle amplification. J Microbiol Methods. Oct. 2011;87(1):38-43.

Isaksson, et al. MLGA—a rapid and cost-efficient assay for gene copy-number analysis. Nucleic Acids Res. 2007;35(17):e115.

Johansson, et al. Targeted resequencing of candidate genes using selector probes. Nucleic Acids Res. Jan. 2011;39(2):e8.

Kinde, et al. Detection and quantification of rare mutations with massively parallel sequencing. Proc Natl Acad Sci U S A. Jun. 7, 2011;108(23):9530-5.

Natsoulis, et al. A flexible approach for highly multiplexed candidate gene targeted resequencing. PLoS One. 2011;6(6):e21088.

Stenberg, et al. PieceMaker: selection of DNA fragments for selector-guided multiplex amplification. Nucleic Acids Res. Apr. 28, 2005;33(8):e72.

Hutchinson, et al., "Cell-free cloning using phi29 DNA polymerase", PNAS, 102:17332-6, 2005.

Ochman, et al., "Genetic applications of an inverse polymerase chain reaction", Genetics, 120:621-3, 1988.

* cited by examiner

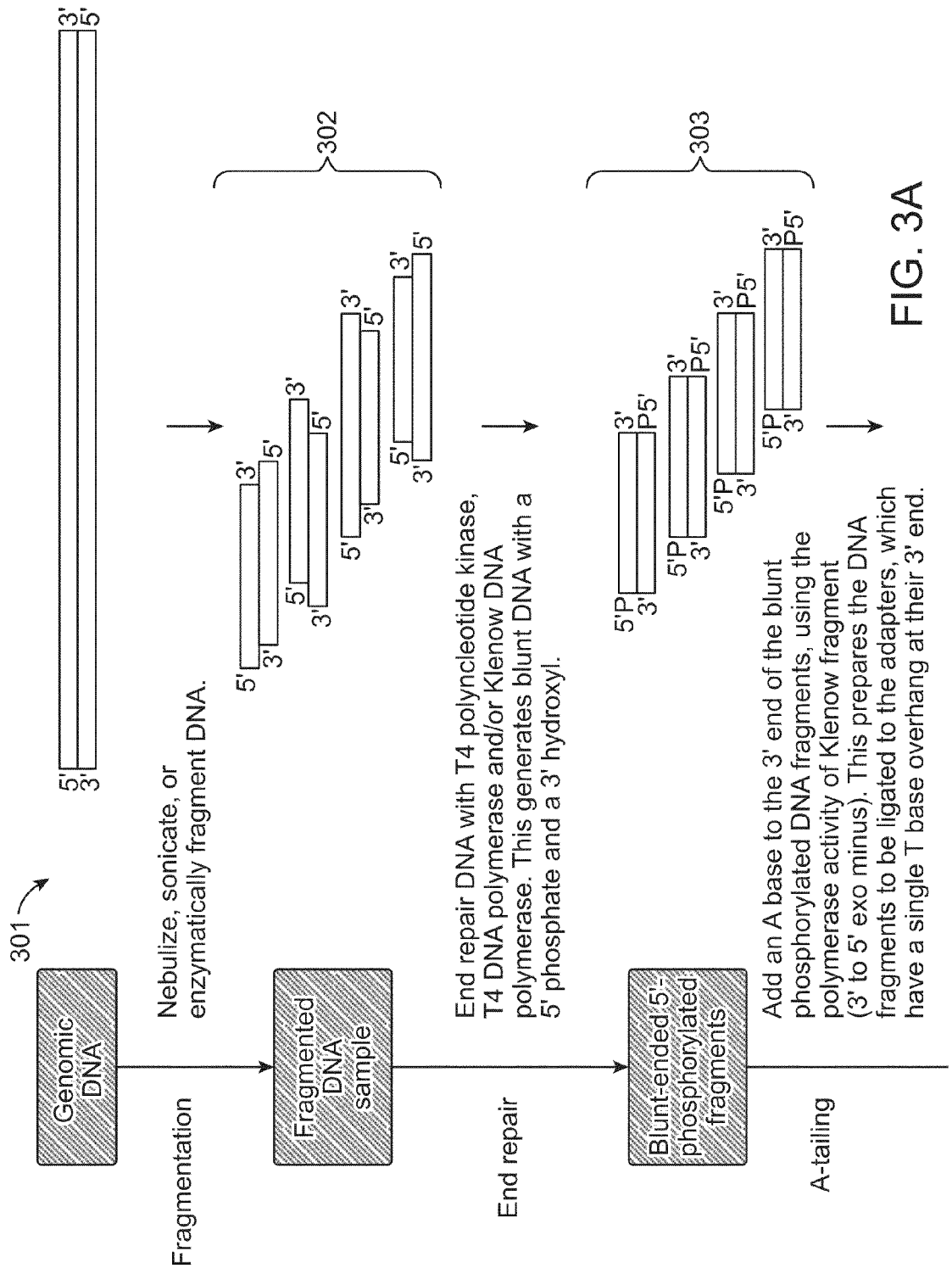

SEQUENCE LISTING

```
<160> NUMBER OF SEQ ID NOS: 7

<210> SEQ ID NO 1
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 1
agtgagtcgc tctgctacgt ctgagtcgga gacacgcagg gatgagatgg cacattcta        59

<210> SEQ ID NO 2
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 2
atgtagaatg tgtctcccta t                                                  21

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide
```

```
<400> SEQUENCE: 3
cgactcacta tagggaga                                                   18

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_difference
<222> LOCATION: 21
<223> OTHER INFORMATION: terminal dideoxy cytosine

<400> SEQUENCE: 4
gacacgcagg gatgagatgg c                                               21

<210> SEQ ID NO 5
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 5
gccatctcat ccctgcgtgt ctccgactca gtctccctat agtgagtcg                 49

<210> SEQ ID NO 6
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 6
cgactcacta tagggaga                                                   18

<210> SEQ ID NO 7
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 7
tctccctata gtgagtcgtg catcgcg                                         27
```

METHODS AND COMPOSITIONS FOR POLYNUCLEOTIDE LIBRARY PRODUCTION, IMMORTALIZATION AND REGION OF INTEREST EXTRACTION

CROSS REFERENCE TO RELATED APPLICATION

This application claims priority from U.S. Provisional Application Ser. No. 61/358,345 filed on Jun. 24, 2010, the entirety of which is incorporated herein by reference.

INTRODUCTION

A major goal in genetics research is to understand the genetic underpinning for complex traits, particularly susceptibilities for common diseases such as diabetes, cancer, hypertension, and the like (see, e.g., Collins et al, Nature, 422: 835-847 (2003)). The draft sequence of the human genome has provided a starting point for this highly complex endeavor. The development of high throughput and/or region-specific genetic analyses will play a key role in facilitating our understanding of how genetics determine or affect states of health and disease.

SUMMARY

Aspects of the present invention are drawn to methods and compositions for the genetic analysis of regions of interest (ROI) from one or more starting polynucleotide sample(s). In certain aspects, adapter tagged polynucleotide fragments from a plurality of initial polynucleotide samples are pooled, circularized and amplified to produce an immortalized library. Multiple ROI's from this immortalized library are amplified (e.g., in independent iPCR reactions) to generate amplicons, and, in some embodiments, pooled to form a pooled ROI amplicon sample. In certain embodiments, the amplicons for each ROI amplicon in the pooled ROI amplicon sample are present at known molar or mass ratios. The pooled ROI amplicon sample can be analyzed/processed as desired, e.g., sequenced using next generation sequencing technology.

BRIEF DESCRIPTION OF THE DRAWINGS

The invention is best understood from the following detailed description when read in conjunction with the accompanying drawings. It is emphasized that, according to common practice, the various features of the drawings are not to-scale. Indeed, the dimensions of the various features are arbitrarily expanded or reduced for clarity. Included in the drawings are the following figures:

FIGS. 3A to 3H show the steps for one exemplary workflow according to aspects of the subject invention.

FIGS. 4A, 4B, 4C and 4D each shows exemplary read strategies for circularization and inverse PCR target enrichment.

DEFINITIONS

Figure 1A:
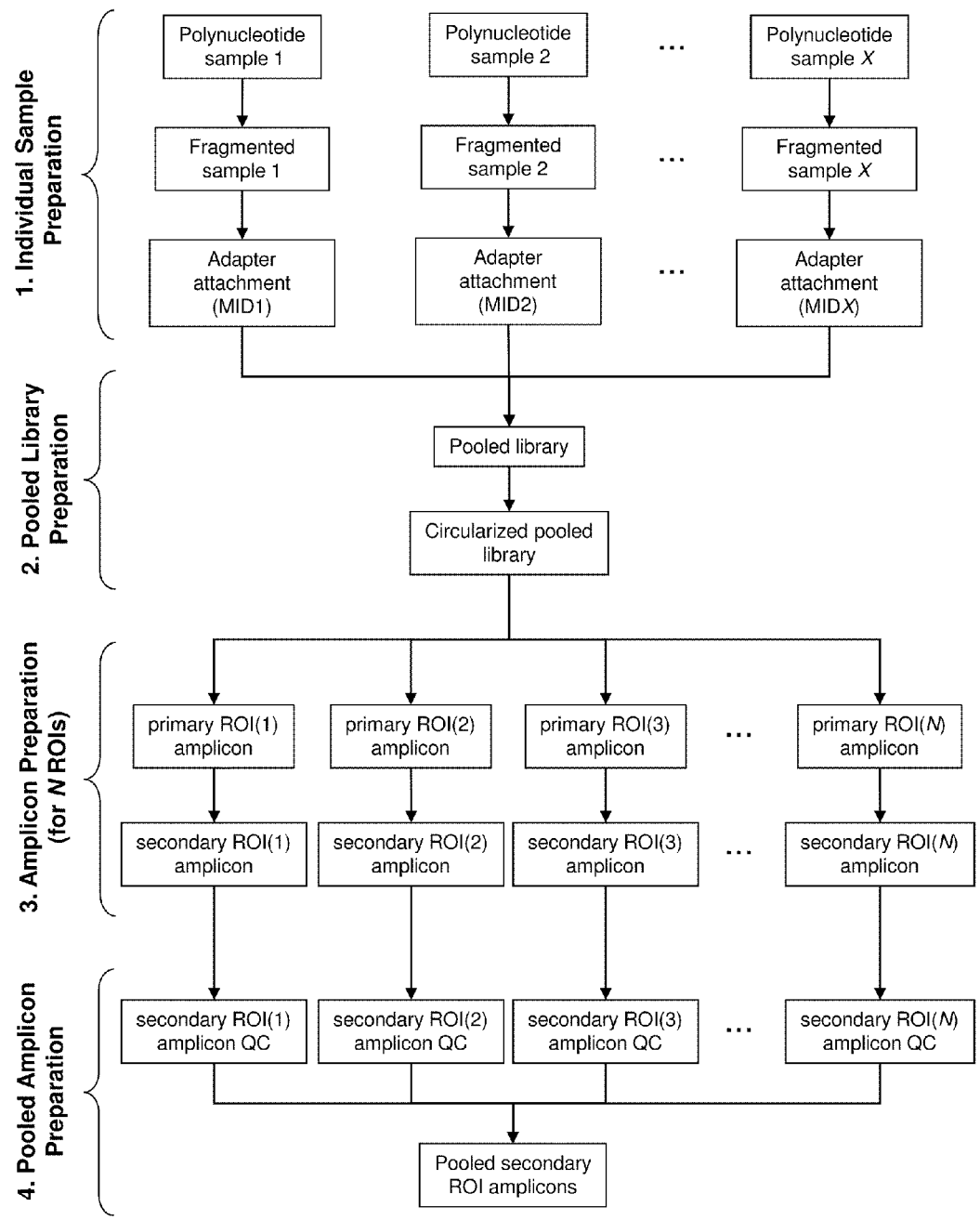
FIGS. 1A and 1B show exemplary workflows depicting a number of process steps according to certain embodiments of the present invention as well as compositions produced by these exemplary process steps and reagents for carrying them out.

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target polynucleotides. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "TAQ-MAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

"Complementary" or "substantially complementary" refers to the hybridization or base pairing or the formation of a duplex between nucleotides or polynucleotides, such as, for instance, between the two strands of a double stranded DNA molecule or between an oligonucleotide primer and a primer binding site on a single stranded polynucleotide. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. A stable duplex can include Watson-Crick base pairing and/or non-Watson-Crick base pairing (e.g., Hoogsteen base pairs) between the strands of the duplex (where base pairing means the forming hydrogen bonds). In certain embodiments, a non-Watson-Crick base pair includes a nucleoside analog, such as deoxyinosine, 2,6-diaminopurine, PNAs, LNA's and the like. In certain embodiments, a non-Watson-Crick base pair includes a "wobble base", such as deoxyinosine, 8-oxo-dA, 8-oxo-dG and the like, where by "wobble base" is meant a nucleic acid base that can base pair with a first nucleotide base in a complementary polynucleotide strand but that, when employed as a template strand for polynucleotide synthesis, leads to the incorporation of a second, different nucleotide base into the synthesizing strand (wobble bases are described in further detail below). A "mismatch" or a "mismatched region" in a duplex between two oligonucleotides or polynucleotides means that at least one pair of nucleotides in the duplex fails to undergo Watson-Crick bonding.

"Genetic region," "region," "region of interest," (ROI) and equivalents in reference to a genome or target polynucleotide, means a sub-region or segment of the genome or target polynucleotide. As used herein, genetic region, region, or region of interest (ROI) may refer to the position of a nucleotide, a gene or a portion of a gene in a genome, including mitochondrial DNA, synthetic DNA or other non-chromosomal DNA (e.g., bacterial plasmid), or it may refer to any contiguous portion of genomic sequence whether or not it is within, or associated with, a gene. A genetic region, region, or region of interest (ROI) can be from a single nucleotide to a segment of a few hundred or a few thousand nucleotides in length or more.

By "isolation", "isolate", "isolating" and the like is meant selecting or separating one or more constituents from others in a sample. "Isolating" thus includes producing a sample that has an increased percentage of one or more constituents of interest from a starting sample (e.g., by positive or negative selection). An isolated sample may contain the constituent(s) of interest at anywhere from 1% or more, 5% or more, 10% or more, 50% or more, 75% or more, 90% or more, 95% or more, 99% or more, and up to and including 100% purity. The terms "enriching", "purifying", "separating", "selecting" and the like, are used interchangeably with "isolating".

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whiteley et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Multiplex Identifier" (MID) as used herein refers to a tag or combination of tags associated with a polynucleotide whose identity (e.g., the tag DNA sequence) can be used to differentiate the polynucleotide from other polynucleotides in a mixture of polynucleotides. In certain embodiments, the MID on a polynucleotide is used to identify the source from which the polynucleotide is derived. For example, a nucleic acid sample may be a pool of polynucleotides derived from different sources, (e.g., polynucleotides derived from different individuals, different tissues or cells, or polynucleotides isolated at different times points), where the polynucleotides from each different source is tagged with a unique MID. As such, a MID provides a correlation between a polynucleotide and its source. In certain embodiments, MIDs are employed to uniquely tag each individual polynucleotide in a sample.

Identification of the number of unique MIDs in a sample can provide a readout of how many individual polynucleotides are present in the sample (or from how many original polynucleotides a manipulated polynucleotide sample was derived; see, e.g., U.S. Pat. No. 7,537,897, issued on May 26, 2009, incorporated herein by reference in its entirety). MIDs can range in length from 2 to 100 nucleotide bases or more and may include multiple subunits, where each different MID has a distinct identity, combination, and/or order of subunits. Exemplary nucleic acid tags that find use as MIDs are described in U.S. Pat. No. 7,544,473, issued on Jun. 6, 2009, and titled "Nucleic Acid Analysis Using Sequence Tokens", as well as U.S. Pat. No. 7,393,665, issued on Jul. 1, 2008, and titled "Methods and Compositions for Tagging and Identifying Polynucleotides", both of which are incorporated herein by reference in their entirety for their description of nucleic acid tags and their use in identifying polynucleotides. In certain embodiments, a set of MIDs employed to tag a plurality of samples need not have any particular common property (e.g., Tm, length, base composition, etc.), as the methods described herein can accommodate a wide variety of unique MID sets. It is emphasized here that MIDs need only be unique within a given experiment. Thus, the same MID may be used to tag a different sample being processed in a different experiment. In addition, in certain experiments, a user may use the same MID to tag a subset of different samples within the same experiment. For example, all samples derived from individuals having a specific phenotype may be tagged with the same MID, e.g., all samples derived from control (or wildtype) subjects can be tagged with a first MID while subjects having a disease condition can be tagged with a second MID (different than the first MID). As another example, it may be desirable to tag different samples derived from the same source with different MIDs (e.g., samples derived over time or derived from different sites within a tissue). Further, MIDs can be generated in a variety of different ways, e.g., by a combinatorial tagging approach in which one MID is attached by ligation and a second MID is attached by primer extension. Thus, MIDs can be designed and implemented in a variety of different ways to track polynucleotide fragments during processing and analysis, and thus no limitation in this regard is intended.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structural Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids ("LNAs"), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target polynucleotide flanked by primer binding sites, such reaction comprising one or more repetitions of the following steps: (i) denaturing the target polynucleotide, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target polynucleotide may be denatured at a temperature >90° C., primers annealed at a temperature in the range 50-75° C., and primers extended at a temperature in the range 68-78° C. The term "PCR" encompasses derivative forms of the reaction, including but not limited to, RT-PCR, real-time PCR, nested PCR, quantitative PCR, multiplexed PCR, inverse PCR and the like. Reaction volumes typically range from a few nanoliters, e.g., 2 nL in a microfluidic device, to a few hundred nanoliters, e.g. 200 nL, to a few hundred μL, e.g. 200 μL. "Inverse PCR" or "iPCR" means a PCR that is performed using a primer pair designed such that primer extension from the primers proceeds away from each another on an un-manipulated target polynucleotide (e.g., genomic DNA) rather than towards each another as in conventional PCR (i.e., the 3' ends of an iPCR primer pair do not face each other on the un-manipulated target polynucleotide; see, e.g., FIG. 4A under "Genomic positions"). Therefore, in order to generate amplicons in an iPCR reaction, the target polynucleotide is manipulated such primer extension proceeds toward one another. Circularization is one exemplary way to manipulate a target polynucleotide to allow for iPCR amplicons to be generated (see, e.g., FIG. 4A under "Circular structure"). Also, concatemeric linear polynucleotides amplified from circularized target polynucleotides (e.g., by rolling circle amplification) are a suitable template to generate iPCR amplicons. In concatemeric target polynucleotides, a first primer of the iPCR primer pair extending from a first copy of the concatamer towards a second copy of the concatamer can generate amplicons with the second primer of the iPCR primer pair extending from the second copy of the concatamer towards the first copy of the concatamer (see FIG. 3C to 3D, which shows exemplary iPCR amplicons generated from concatameric target polynucleotides). Exemplary iPCR protocols are described in U.S. Pat. No. 4,994,370 to Silver et al. and titled "DNA amplification technique", incorporated herein by reference in its entirety. "Reverse transcription PCR," or "RT-PCR," means a PCR that is preceded by a reverse transcription reaction that converts a target RNA to a complementary single stranded DNA, which is then amplified, see e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g., Gelfand et al., U.S. Pat. No. 5,210,015 ("TAQMAN™"); Wittwer et al., U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. With respect to PCR primer pairs designed to generate amplicons that include all or part of a polynucleotide region of interest (ROI as described above), the primer pair may be referred to as "targeting the ROI". While a PCR primer pair "targets a ROI", the amplicons produced using the PCR primer pair may include sequences other than the ROI, including, for example, genomic sequences adjacent to the ROI, adapter sequences, synthetic primer sequences, etc. Moreover, a PCR primer pair that targets a ROI may not hybridize to sequences within the ROI itself. For example, a PCR primer pair may include a first primer that binds to a genomic sequence adjacent to a ROI and a second primer specific for an adapter sequence.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" as used herein refer to linear polymers of nucleotide monomers. Polynucleotides and oligonucleotides can have any of a variety of structural configurations, e.g., be single stranded, double stranded, or a combination of both, as well as having higher order intra- or intermolecular secondary/tertiary structures, e.g., hairpins, loops, triple stranded regions, etc. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, wobble base pairing, or the like. As described in detail below, by "wobble base" is meant a nucleic acid base that can base pair with a first nucleotide base in a complementary polynucleotide strand but that, when employed as a template strand for nucleic acid synthesis, leads to the incorporation of a second, different nucleotide base into the synthesizing strand. Such monomers and their internucleosidic linkages may be naturally occurring or may be analogs thereof, e.g. naturally occurring or non-naturally occurring analogs. Non-naturally occurring analogs may include peptide nucleic acids (PNAs, e.g., as described in U.S. Pat. No. 5,539,082, incorporated herein by reference), locked nucleic acids (LNAs, e.g., as described in U.S. Pat. No. 6,670,461, incorporated herein by reference), phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that, upon forming a duplex with a polynucleotide template, is capable of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. Generally, a double-stranded primer is treated to separate its strands before being used in the preparation of extension products. This denaturation step is typically affected by heat, but may alternatively be carried out using alkali, followed by neutralization. Thus, a "primer" hybridizes to a complementary site of a template strand (e.g., by hydrogen bonding) to give a primer/template complex suitable for initiation of nucleic acid synthesis by a polymerase. During nucleic acid synthesis, the primer is extended by the successive, covalent addition bases to its 3' end that are complementary to the template strand.

A "primer pair" as used herein refers to first and second primers having nucleic acid sequence suitable for nucleic acid-based amplification of a target polynucleotide or region thereof. Such primer pairs generally include a first primer having a sequence that is the same or similar to that of a first portion of a target polynucleotide, and a second primer having a sequence that is complementary to a second portion of a target polynucleotide to provide for amplification of the target polynucleotide or a region thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

It is noted that primers employed in a nucleic acid synthesis reaction may include an unpaired region at the 5' end, also referred to herein as a "tail", which will be incorporated into the nucleic acid product of the synthesis reaction. Tailed primers may be used to add specific domains to a polynucleotide of interest as desired, e.g., sequencing primer sites, MIDs, reflex sites, circularization domains, etc.

"Reflex site", "reflex sequence" and equivalents are used to indicate one or more sequences present in a polynucleotide that are employed to move a domain intra-molecularly from its initial location to a different location in the polynucleotide. The use of reflex sequences is described in detail in PCT application IB2010/002243, filed on Aug. 13, 2010 (published as WO 2011/021102), and entitled "Compositions and Methods for Intramolecular Nucleic Acid Rearrangement Using Reflex Sequences", incorporated herein by reference. In certain embodiments, a reflex sequence is chosen so as to be distinct from other sequences in the polynucleotide (i.e., with little sequence homology to other sequences likely to be present in the polynucleotide, e.g., genomic or sub-genomic sequences to be processed). As such, a reflex sequence should be selected so as to not hybridize to any sequence except its complement under the conditions employed in the reflex processes. The reflex sequence may be a synthetic or artificially generated sequence (e.g., added to a polynucleotide in an adapter domain) or a sequence present normally in a polynucleotide being assayed (e.g., a sequence present within a region of interest in a polynucleotide being assayed). In the reflex system, a complement to the reflex sequence is present (e.g., inserted in an adapter domain) on the same strand of the polynucleotide as the reflex sequence (e.g., the same strand of a double-stranded polynucleotide or on the same single stranded polynucleotide), where the complement is placed in a particular location so as to facilitate an intramolecular binding and polymerization event on such particular strand. Reflex sequences employed in the reflex process described herein can thus have a wide range of lengths and sequences. Reflex sequences may range from 5 to 200 nucleotide bases in length.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature (e.g., as measured in ° C.) at which a population of double-stranded polynucleotide molecules becomes half dissociated into single strands. Several equations for calculating the $T_m$ of nucleic acids are known in the art (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of $T_m$.

"Sample" means a quantity of material from a biological, environmental, medical, patient, or other source in which detection, measurement, or labeling of an analyte, e.g., one or more target nucleic acids, is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "upstream" and "downstream" in describing relative positions of nucleotides or nucleotide domains in a polynucleotide and/or polymerization are used herein as understood by one of skill in the art. As such, "downstream" generally means proceeding in the 5' to 3' direction, i.e., the direction in which a nucleotide polymerase normally extends a sequence, and "upstream" generally means the converse. For example, a first primer that hybridizes "upstream" of a second primer on the same target polynucleotide molecule is located on the 5' side of the second primer (and thus nucleic acid polymerization from the first primer proceeds towards the second primer).

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It is noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and Compositions

Figure 1B:
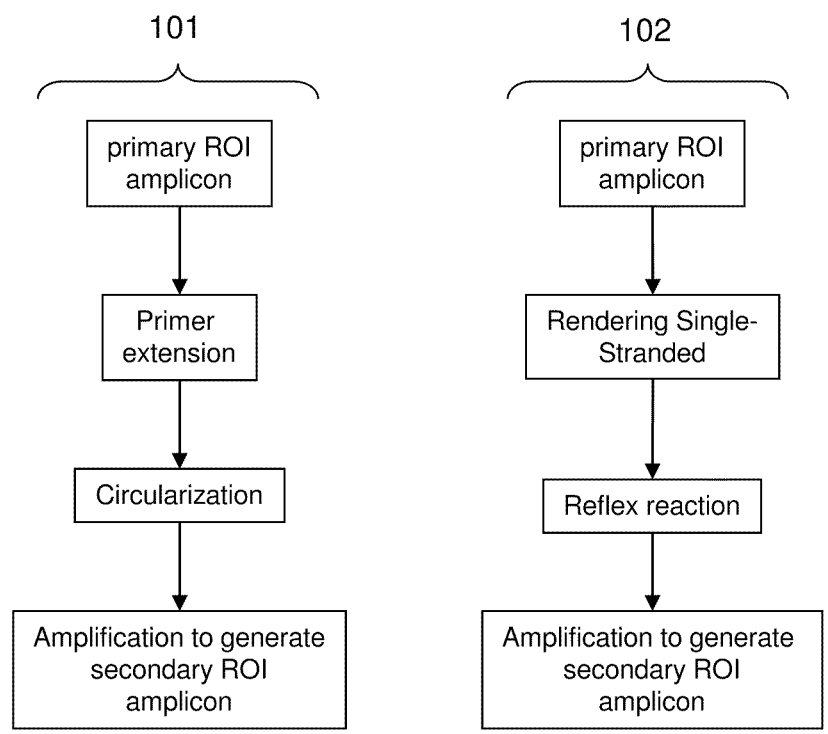

FIGS. 1A and 1B show exemplary workflows depicting a number of process steps according to certain aspects of the present invention. Compositions produced by these exemplary process steps and reagents for carrying them out are also shown. It is noted here that other embodiments are encompassed by the present invention in which one or more of the steps shown in FIGS. 1A and 1B are not performed and/or additional steps not shown in FIGS. 1A and 1B are included. In general, the desires of the user of the subject invention will influence which specific steps to perform and the order in which they are carried out, and thus no limitation in this regard in intended.

The exemplary workflow in FIG. 1A is broken down into 4 elements: 1. individual sample preparation for X number of polynucleotide samples, 2. pooled library preparation, 3. amplicon preparation for N regions of interest (ROIs) (where N is the number of different ROIs being amplified), and 4. pooled amplicon preparation. These elements of the workflow will be summarized below and then described in further detail with reference to subsequent figures.

In step 1 of FIG. 1A, multiple individual polynucleotide samples (i.e., polynucleotide samples 1 to X) are processed separately to add adapters that include one or more desired domains that find use in subsequent steps (e.g., primer binding sites, reflex sites, circularization sites, polymerase recognition sequences, MID, degenerate base region (DBR), and the like, as described in further detail below). Step 1 includes fragmenting each of the polynucleotide samples and attaching an adapter to each fragmented sample, where the adapter includes a sample-specific MID (i.e., MID1 for sample 1, MID2 for sample 2, all the way to MIDX for sample X). As noted in the definition section above, MIDs having a variety of different structural features may be employed, including combinatorial MIDs having multiple distinct domains on the tagged fragment (e.g., two distinct MID domains present on opposite ends of an asymmetrically tagged fragment). Polynucleotides in a sample being analyzed (or processed) in accordance with the present invention can be from any source. As such, polynucleotides in a sample include, but are not limited to, genomic DNA, complementary DNA (cDNA), RNA (e.g., messenger RNA, ribosomal RNA, short interfering RNA, microRNA, etc.), plasmid DNA, mitochondrial DNA, synthetic DNA, etc. Furthermore, any organism, organic material or nucleic acid-containing substance can be used as a source of nucleic acids to be processed in accordance with the present invention including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the nucleic acids in the nucleic acid sample are derived from a mammal, where in certain embodiments the mammal is a human.

In certain embodiments, polynucleotides from an initial sample (or multiple samples) are enriched for a subset of polynucleotides to produce one or more enriched samples. The term "enriched" is used herein to refer to any process that reduces the complexity of polynucleotides in a sample, generally by increasing the relative concentration of particular polynucleotide species in the sample (e.g., having a specific region of interest, including a specific polynucleotide sequences such as mitochondrial DNA, certain expressed regions, etc., lacking a region or sequence, being within a specific size range, etc.). In certain embodiments, enriching can include removing specific polynucleotides having an undesirable sequence or feature, e.g., polynucleotides that include frequently occurring repeat sequences. There are a wide variety of ways to enrich polynucleotides having a specific characteristic(s) or sequence, and as such any convenient method to accomplish this may be employed (see, e.g., Mamanova et al. 2010, Nature Methods vol. 7, pp. 111-118; and Shagina et al. 2010, Biotechniques vol. 48(6) pp. 455-459).

It is noted that an enrichment (or complexity reduction) step can take place at any step in the process, and will be determined by the desires of the user. For example, enrichment can take place in individual source-specific samples (e.g., untagged polynucleotides prior to adapter ligation) or in multiplexed samples (e.g., polynucleotides tagged with MIDs and pooled).

Fragmentation of the polynucleotides in each sample may be accomplished in any convenient manner, including sequence specific fragmentation, e.g., at specific restriction enzyme cut sites (e.g., using one or more restriction endonucleases) or at "random" sites, using, e.g., enzymes, nebulization, ultrasonic disruption, etc. In certain embodiments (and as described below), modification of the ends of the fragments may be needed to prepare the ends for ligation to adapter fragments having a compatible ligation site. Preparing the ends of fragments for ligation, e.g., to an adapter, plasmid, other fragments, etc., is sometimes referred to herein as "polishing" (as in "fragment ends are polished prior to ligation to adapters"). The term "polished" (or equivalents) is used herein to mean a process for producing ends on a nucleic acid fragment (or fragments) that are suitable for ligation or attachment to another nucleic acid fragment (e.g., an adapter). As such, polishing refers to any step or steps used to produce ligation-compatible ends. Ligation-compatible ends may have any configuration, e.g., be blunt ends, recessed ends or overhangs, such terms being well known in the art. In certain embodiments, various steps in this process may be combined such as in the Nextera transposon system from Epicentre Technologies, Madison, Wis.

In certain other embodiments, end repair is not needed (e.g., when fragmentation is accomplished with a sequence-specific restriction enzyme that leaves ligation compatible ends for the adapter being used).

It is noted here that in certain embodiments, a polynucleotide sample does not undergo fragmentation prior to repair and/or adapter attachment. For example, a sample comprising cDNAs, amplicons or mixtures of amplicons (e.g., PCR products), or other polynucleotides of an appropriate size range for subsequent process steps, need not be fragmented prior to adapter attachment.

Ligation-compatible ends (e.g., of a fragment and an adapter) can be ligated to one another under appropriate ligation conditions, for example in the presence of an enzyme having DNA ligase activity in appropriate buffering conditions and co-factors. Where a single stranded polynucleotide is employed, a double stranded adapter construct that possesses an overhang configured to bind to the end of the single-stranded polynucleotide can be used. Alternatively, an enzyme can be used which will ligate together ssDNA. In another alternative, the end of a single stranded polynucleotide can be modified to include specific nucleotide bases that are complementary to the overhang in the double stranded adapter (e.g., using terminal transferase). Compatible ends on double stranded fragments may also be produced by the addition of one or more nucleotide [e.g., using Klenow fragment lacking 3'-5' exonuclease activity in the presence of specific nucleotide(s), by the controllable addition of nucleotides using terminal transferase (see, e.g., Schmidt et al., Nucleic Acids Research, 1999, v. 27, pe31), and the like].

Any convenient adapter may be used, where the adapter may contain one or more domains that find use in subsequent steps of a workflow. Non-limiting examples of adapter domains include primer binding sites (e.g., for sequencing or amplification), reflex sites, circularization sites, polymerase recognition sequences, and MID and the like, as described in further detail below. Construction of adapters may be achieved in any convenient manner.

In certain embodiments, it is beneficial to generate polynucleotides that are asymmetrically tagged, meaning that the left and right adapters on a particular single-stranded segment of DNA are not identical. This process is referred to generically as attaching adapters asymmetrically. Production of polynucleotides having asymmetric adapters may be achieved in any convenient manner. Exemplary asymmetric adapters are described in: U.S. Pat. Nos. 5,712,126 and 6,372,434; U.S. Patent Publications 2007/0128624 and 2007/0172839; and PCT publication WO/2009/032167; all of which are incorporated by reference herein in their entirety. In certain embodiments, the asymmetric adapters employed are those described in U.S. patent application Ser. No. 12/432,080, filed on Apr. 29, 2009, incorporated herein by reference in its entirety.

As one example, a user of the subject invention may use an asymmetric adapter to tag polynucleotides. An "asymmetric adapter" is one that, when ligated to both ends of a double stranded nucleic acid fragment, will lead to the production of primer extension or amplification products that have non-identical sequences flanking the fragment. The ligation is usually followed by subsequent processing steps so as to generate the non-identical terminal adapter sequences. Thus, replication of an asymmetric adapter-attached double stranded fragment(s) results in polynucleotide products in which there is at least one nucleic acid sequence difference, or nucleotide/nucleoside modification, between the terminal adapter sequences. Attaching adapters asymmetrically to polynucleotides (e.g., polynucleotide fragments) results in fragments that have one or more adapter sequences on one end (e.g., one or more adapter domain, e.g., a primer binding site) that are either not present or have a different nucleic acid sequence as compared to the adapter sequence on the other end. It is noted that an adapter that is termed an "asymmetric adapter" is not itself structurally asymmetric, nor does the mere act of attaching an asymmetric adapter to a polynucleotide fragment render it immediately asymmetric. Rather, an asymmetric adapter-attached double stranded polynucleotide, which has an identical asymmetric adapter at each end, produces replication products that are asymmetric with respect to the adapter sequences on opposite ends (i.e., after at least one round of amplification/primer extension). It is further noted that in certain embodiments, denaturing an asymmetric adapter-attached double-stranded polynucleotide produces asymmetrically tagged single stranded polynucleotides. Such single stranded asymmetrically tagged polynucleotides may be manipulated in accordance with aspects of the present invention, e.g., subjected to circularization and amplification, without first being replicated. In certain embodiments, an asymmetric adapter can be used to place different MID regions on opposite ends of each fragment in a sample, also called combinatorial tagging.

Exemplary asymmetric adapters, including combinatorial asymmetric adapters, are shown in FIGS. 2A to 2D (described in further detail below).

Any convenient asymmetric adapter, or process for attaching adapters asymmetrically, may be employed in practicing the present invention. Exemplary asymmetric adapters are described in: U.S. Pat. Nos. 5,712,126 and 6,372,434; U.S. Patent Publications 2007/0128624 and 2007/0172839; and PCT publication WO/2009/032167; all of which are incorporated by reference herein in their entirety. In certain embodiments, the asymmetric adapters employed are those described in U.S. patent application Ser. No. 12/432,080, filed on Apr. 29, 2009, incorporated herein by reference in its entirety.

As shown in FIG. 1A, a plurality of polynucleotide samples ("multiple polynucleotide samples" in FIG. 1A) are analyzed in aspects of the present invention, where by "plurality" is meant 2 or more, e.g., 2 or more, 3 or more, 5 or more, 10 or more, 50 or more, 100 or more, 500 or more, 1000 or more, 5000 or more, up to and including about 10,000 or more. No limitation in this regard is intended. Where a plurality of samples are analyzed, adapters for tagging the polynucleotides from each original sample include a multiplex identifier (MID) such that the source from which each tagged polynucleotide fragment was derived can be determined (see description and exemplary uses of MIDs above).

After individual sample preparation (step 1 of FIG. 1A), a pooled library is prepared in step 2 by combining adapter attached fragments from each of the multiple polynucleotide samples into a single sample. This pooled library is then subjected to an intra-molecular ligation reaction to circularize the pooled library fragments thereby producing a circularized pooled library. Any convenient method for polynucleotide fragment circularization may be employed, which may rely on sequences present in the adapter regions of the polynucleotide fragments. As one non-limiting example (and as described further below), fragments may be circularized by hybridizing them to a "circularization oligonucleotide" that brings the 5' phosphate and 3' hydroxyl ends of each fragment into proximity for subsequent ligation. Alternate methods include the use of 'selector probes' or 'inversion probes' that can bind to adapter sequences and circularize the templates (e.g., by ligation, by DNA polymerization, or by a combination of both). The design and use of exemplary selector probes are described in Dahl et al., Nucleic Acids Research "Multiplex amplification enabled by selective circularization of large sets of genomic DNA fragments" Nucleic Acids Research 2005 33(8):e71 (incorporated herein by reference). The design and use of exemplary inversion probes are described in Absalan et al. "Molecular Inversion Probe Assay" Methods in Molecular Biology 2008, 396 pp. 315-330 (incorporated herein by reference). Different ligases may be used in the context of the circularization reactions including, but not limited to, Taq DNA ligase, T4 DNA ligase, *Escherichia coli* DNA ligase, etc. Following the ligation to make circular it is usually advisable to remove the "circularization oligonucleotide" (also known as the "splint") by SPRI cleanup or by use of exonuclease treatment (e.g., exonuclease I and/or exonuclease III). It may also be useful to employ a phosphatase such as shrimp alkaline phosphatase to destroy any potentially reactive nucleotide tri-phosphates, such as ATP from the ligation reaction, so that subsequent processing steps are not affected.

Alternatively, the polynucleotide fragments could be made double-stranded, e.g. by primer extension on adapter tagged molecules, and then subsequently self-ligated. Another method would be to use a recombinase system to produce circular polynucleotide fragments (e.g., Cre-Lox system; e.g., by including Lox sites in adapters of the polynucleotide fragments).

In certain embodiments, a pooled sample may be subjected to additional or alternative process steps prior to circularization. For example, a pooled library of asymmetrically-tagged fragments may be selected for a specific size range to generate a size-selected library using any convenient method. Exemplary size-selection methods include solid-phase reversible immobilization (SPRI) high and low cut-off (see, e.g., Lennon et al., 2000), electrophoretically-driven size selection (e.g., as employed in LabChip XT from Caliper Life Sciences), or any other convenient method.

In certain embodiments (not shown in FIG. 1A), the circularized pooled library is subjected to an amplification reaction, e.g., using phi29 DNA polymerase, to generate an immortalized pooled library (discussed in detail below; see, e.g., FIG. 3C). As noted above, specific domains present in the adapters facilitate certain steps in the process, e.g., one or more primer binding sites for use during phi29 DNA polymerization.

In general, an "immortalized" library (or sample) is one from which copies can be made without consuming the original sample, akin to producing a "master copy" of a document from which photocopies can be made indefinitely. For example, an immortalized sample can be produced by immobilizing adapter-ligated fragments to a solid substrate, where the adapter includes a synthesis primer binding site. Such immobilized fragments can be used to produce copies of the fragments by primer extension using the adapter primer binding site. These copies can be eluted from the immobilized fragments for subsequent manipulation. The immobilized adapter ligated fragments can then be used to produce more copies.

In certain embodiments, an immortalized sample is a sample that allows an indefinite number of sequential copies to be produced. This is akin to making copies from previous copies, for example as in producing a copy of a copy of an original electronic file. For example, a sample of polynucleotide fragments that include PCR primer binding sites on both ends (e.g., present in adapter sequences ligated to the fragments) can be PCR amplified to produce a first copy of the fragments, the first copy can be PCR amplified to produce a second copy, etc. Other functional sites in adapter sequences on the terminal ends of nucleic acid fragments can also be used to produce immortalized samples (e.g., T3, SP6 and/or T7 RNA polymerase binding sites, e.g., where a T3 site is in an adapter on a first end of a polynucleotide fragment and a T7 site is in the adapter at the opposite end of the fragment; unique DNA polymerase binding sites; hairpin adapters to create circular DNA that can be amplified by rolling circle amplification; or components of cellular replication systems, e.g. bacterial plasmids).

In certain embodiments, an adapter ligated sample includes functional domains that allow it to be immortalized both of the ways described above (i.e., such that the original adapter ligated sample can be copied indefinitely and such that the resultant copies can be copied sequentially). In addition, an immortalized library may be produced at any step, or at multiple different steps, during the workflow, e.g., directly from the polynucleotides derived from a particular source, after MID tagging, after production of a pooled polynucleotide sample (combining MID tagged polynucleotides from different sources), after an enrichment or isolation step (e.g., region of interest extraction, as detailed below), etc. In essence, the point at which to generate an immortalized sample is dependent on the desires of a user. For example, one could add a specific functional domain onto a polynucleotide of interest using a tailed primer in an extension reaction at any point in the workflow.

As shown in FIG. 1A, the circularized pooled library (or an immortalized pooled library generated therefrom) of step 2 is used for amplicon preparation for N regions of interest (ROIs) in step 3. A polynucleotide ROI in a polynucleotide sample is any region or locus for which analysis is desired by a user, e.g., a genomic region, a region corresponding to an expressed sequence (e.g., from an mRNA), a synthetically produced region, etc. In step 3 of FIG. 1A, ROI amplicon preparation is broken down into two parts: producing a primary ROI amplicon and producing a secondary ROI amplicon, both of which are discussed in further detail below.

As shown in step 3 of FIG. 1A, amplicon preparation for each ROI being performed is done in an independent reaction (or reactions) (i.e., for ROI(1), ROI(2), ROI(3)... to ROI(N)). However, it is noted here that in certain embodiments, more than one ROI may be produced in a single reaction, e.g., using a multiplex amplification reaction (e.g., multiplex PCR). Further, the number and identity of the one or more ROI will be determined by the desires of the user, and as such, no limitation in this regard is intended. In certain embodiments, the number of ROIs ranges from 2 to 10,000 and anywhere in between, including but not limited to, from 5 to 5,000, from 20 to 2,000, from 100 to 1,000, and so on.

Any convenient method for performing amplification reactions to produce ROI amplicons (e.g., the primary and secondary ROI amplicons as in FIG. 1A) can be used in practicing the subject invention. In certain embodiments, the amplification reaction performed is a PCR, such reactions being known in the art (e.g., standard PCR, inverse PCR, and the like). In certain embodiments, an amplification reaction will only produce the desired amplification product, e.g., a primary ROI amplicon, from circularized polynucleotides (or amplification products generated from circularized templates, e.g., concatenates made by rolling circle amplification of circular polynucleotides as discussed below). In certain embodiments, the nucleic acid polymerase employed in the amplification reaction is a polymerase that has proofreading capability and/or nucleic acid strand-displacing activity (e.g., phi29 DNA Polymerase, *Thermococcus litoralis* DNA polymerase, *Pyrococcus furiosus* DNA polymerase, etc.). Further, a group of replicating enzymes, also called replisomes, may be employed. In certain other embodiments, non-proofreading polymerases are employed.

It is further noted that additional processing steps or analysis can be performed after ROI amplification but before performing subsequent steps in the workflow shown in FIG. 1A. Such additional processing or analysis steps are up to the desires of the user.

In embodiments where the multiple polynucleotide samples are fragmented in a random fashion (i.e., not using sequence specific restriction enzyme digestion), the primary ROI amplicons for each ROI may be structurally variable. "Structurally variable" amplicons are those in which the primer binding sites for the PCR primers (e.g., the iPCR primers targeting the ROI) are fixed in genomic space while the adapter sequences are not fixed in genomic space. Thus, in structurally variable amplicons the primer binding sites are at a variable distance from the adapter sequences in each of the amplicons in the population of amplicons. In other words, the variability of structurally variable amplicons is derived from the differences in the polynucleotide sequence (e.g., genomic sequence) interposed between the primer binding sites and the adapter sequences in each individual amplicon of the population of amplicons. For example, structurally variable primary ROI amplicons are produced in iPCRs performed on circularized libraries generated from randomly fragmented genomic DNA. In certain embodiments, the structurally variable ROI amplicons are converted to structurally defined ROI amplicons for use in subsequent process steps (sometimes referred to herein as secondary ROI amplicons). "Structurally defined" amplicons are those in which both the primer binding sites for the PCR primers (e.g., the iPCR primers targeting the ROI) and the adapter sequences are fixed in genomic space. In other words, in structurally defined amplicons the primer binding sites and the adapter sequences in each individual ROI amplicon in the population of ROI amplicons is at a known genomic location. In some cases, structurally defined amplicons also have a known length of the ROI-containing polynucleotide, i.e., the boundaries of the ROI-containing polynucleotide in the amplicons are known (see, e.g., FIG. 2E, described in detail below).

It is noted here that the structurally defined amplicons will sometimes include polynucleotide sequences from a desired ROI with one or more genetic variation as compared to the wildtype sequence for the ROI (e.g., polymorphism, mutation, deletion, insertion, etc.). Thus, structurally defined amplicons from a single ROI may include amplicons that have variable sequence and/or absolute length due to genetic variation of the ROI in the polynucleotides present in the sample, e.g., due to the presence of different alleles, SNPs, mutations, etc. It is further noted that the structurally defined amplicons for each different ROI (e.g., done in different amplification reactions) may have different lengths. The length or range of lengths of each structurally defined amplicon is based on the design of the amplification process used to generate them, and thus up to the user. In certain embodiments, the structurally defined amplicons from each different ROI amplification reaction have lengths that fall within a specified range as well as one or more adapter domain positioned in a manner useful for subsequent processing and/or analysis. For example, if the structurally defined amplicons are to be subjected to next generation sequencing reactions, the length of each different structurally defined amplicon (e.g., secondary ROI(1) amplicon, secondary ROI(2) amplicon, secondary ROI(3) amplicon, to secondary ROI(N) amplicon, as shown in FIG. 1A) can be tailored to be within a size range (or have a similar length) and to have the appropriately placed sequencing primer binding sites. In certain embodiments, the lengths of the secondary amplicons are from 50 to 5000 bases, e.g., from 70 to 3000 bases, from 100 to 2000 bases, from 300 to 1000 bases, etc.

FIG. 1B shows two exemplary processes for obtaining the structurally defined amplicons (e.g., secondary amplicons as in FIG. 1A) by employing either a reflex process (steps on the right, 102) or another round of circularization (steps on the left, 101). It is again noted that in certain embodiments, primary amplicons are structurally defined and need not be subjected to additional manipulation to produce secondary amplicons.

In exemplary process steps 102, each primary ROI amplicon is rendered single-stranded, subjected to a reflex process, and PCR amplified to generate the secondary ROI amplicon. In certain embodiments, one primary amplicon may end up being used as the template for more than one secondary ROI amplicon.

In certain embodiments, single-stranded DNA is isolated before performing the reflex process (although this is not required). Isolation of single-stranded DNA may be achieved in any convenient manner. In certain embodiments (and as detailed below), the primary ROI amplicon is modified on one strand of the duplex with a first member of a binding partner pair, or binding moiety (e.g., biotin), which allows for attachment of one strand of the double stranded amplicon to a solid support or substrate (e.g., a bead, pin, column, plate, etc.) to which is attached the binding partner of the binding moiety (e.g., streptavidin). Binding moieties and their corresponding binding partners are also referred to herein as binding partner pairs. Any convenient binding partner pairs may be used, including but not limited to biotin/avidin (or streptavidin), antigen/antibody pairs, or any of a variety of other chemical and/or non-chemical binding partner pairs (e.g., using any combination of protein, nucleic acid, carbohydrate, lectin, and/or magnetic moieties, etc.). Elution of polynucleotide strands hybridized to the substrate-bound polynucleotides (e.g., by heat or alkaline denaturation or exonuclease treatment, etc.) allows isolation of single stranded DNA amplicon samples (one sample for each ROI being amplified). In certain embodiments, the single DNA strand attached to the beads is isolated and employed in subsequent steps. It is noted here that any convenient single strand isolation technique can be employed, and as such no limitation in this regard is intended. For example, a phosphorothioate linkage can be introduced into one strand of the primary ROI amplicon (e.g., by including it in the 5' end of one of the primers used to generate the amplicon) after which the primary ROI amplicon can be treated with an exonuclease which will degrade the non-modified strand, e.g. T7 and/or lambda exonucleases.

In the embodiment shown in 102, the amplicon that has been rendered single stranded from each different amplification reaction is subjected to a reflex reaction, which is made possible by including reflex sequences in the adapter used for the original tagging of the fragments. Reflex sequences find use in performing intramolecular rearrangement to place a region of interest in proximity to a functional domain (e.g., a domain in an adapter, e.g., a primer binding site or MID). The reflex process is described in detail in PCT application IB2010/002243, filed on Aug. 13, 2010 (published as WO 2011/021102), and entitled "Compositions and Methods for Intramolecular Nucleic Acid Rearrangement Using Reflex Sequences", incorporated herein by reference.

Again, it is noted here that single-stranded DNA isolation is not necessary in order to perform the reflex reaction. Specifically, reaction conditions may be employed that strongly favor the intramolecular reflex reaction in a sample containing both the reflex target sequence and its complement. Thus, in certain embodiments, a reflex reaction can be performed without the need for a single strand DNA isolation process (e.g., a biotin-streptavidin pull-down).

If primers from the amplification reaction that produced the primary ROI amplicons (e.g., the PCR primers) are present in the primary amplicon sample, they should preferably be removed prior to performing the reflex reaction (it is noted that certain single strand DNA isolation processes will also remove primers, and so in these embodiments, no extra step is needed for this purpose). Primer removal can be done using any convenient method, including enzymatically (e.g., ExoSAPit, USB Corporation) or by physical separation (e.g., Agencourt SPRI beads, Beckman Coulter Genomics) and/or dilution.

Once the reflex reaction has been performed, the reflex reaction product is then subjected to an amplification reaction (e.g., a PCR reaction) to generate the secondary ROI amplicons for each ROI (1, 2, 3, to N), which, as described above, are structurally defined.

In exemplary steps 101 of FIG. 1B, the primary ROI amplicons are processed to secondary ROI amplicons by performing a primer extension reaction, followed by intramolecular circularization and performing an amplification reaction to produce the secondary ROI amplicon.

In general, the primer extension reaction (e.g., PCR or linear primer extension reaction) is designed to produce polynucleotide products that can be circularized, e.g., as described above. In certain embodiments, the extension products have defined 5' and 3' terminal sequences that hybridize to a circularization oligonucleotide and have a 5' phosphate (which allows ligation). 5' phosphorylation can be done by using an extension primer having a 5' phosphate or by enzymatic phosphorylation of the extension products. In other embodiments, PCR products, or primer extension products that are rendered double-stranded, can be circularized by blunt ligation. After circularization of the extension products (by any convenient method), the circularized products are amplified (e.g., by PCR) to generate secondary ROI amplicons (as described above for process 102).

In FIG. 1A, an exemplary process for preparing pooled secondary amplicons is shown in step 4. Specifically, after the production of the secondary ROI amplicons (e.g., using either process 101 or 102 as outlined above), and after any desired intermediate steps, each of the secondary ROI amplicons are subjected to quality control analysis (QC) to determine: 1) whether each secondary ROI amplicon has the predicted size; and 2) the secondary ROI amplicon concentration (or amount). It is noted that any convenient amplicon QC analysis or combination of amplicon QC analyses may be employed, including any one or more of size, amount, diagnostic restriction enzyme digestion, double stranded DNA melting analysis, etc. Such QC determinations can be accomplished in any convenient manner.

It is further noted that in certain embodiments, primary amplicons are subjected to further analysis without the production of secondary amplicons. In such embodiments, primary amplicons can be subjected to QC analysis as desired by the user, e.g., for any one or more of size, amount, diagnostic restriction enzyme digestion, double stranded DNA melting analysis, etc.

For example, the amplification reactions to generate the secondary ROI amplicons may be quantitative amplification reactions that provide quantity data for the products during the reaction (e.g., qPCR using labeled PCR primer). Alternatively, the determination can be accomplished by quantitating the secondary ROI amplicons by observing them by such exemplary methods as gel electrophoresis techniques, capillary electrophoresis techniques, microfluidic measurement systems, use of fluorescent dyes which quantify nucleic acid present, or by spectrophotometric analysis, etc.

Upon completing the QC analysis of each of the secondary ROI amplicons, a pooled sample containing the secondary ROI amplicons, also called a normalized sample, can be produced and employed in subsequent processing steps and/or analysis. By "normalized sample" is meant that the different species of secondary ROI amplicons in the sample are present at known molar ratios. "Normalized" is not limited to mean that the polynucleotide species are present at the same (or substantially the same) amount or concentration, although such embodiments are encompassed by this term. Thus, in certain embodiments, the products are mixed such that the concentration or amount of each secondary ROI amplicon is substantially equivalent in the normalized sample, whereas in other embodiments, the products are mixed such that the concentration or amount of one or more specific secondary ROI amplicon is less than one or more other specific secondary ROI amplicon in the sample. No limitation in this regard is intended. Exemplary normalization methods and compositions may be found in PCT application serial number IB/2011/000573, filed on Feb. 14, 2011, and incorporated herein by reference in its entirety.

The pooled secondary ROI amplicon sample is a reduced complexity sample that includes structurally defined amplicons from a multiplicity of different ROIs wherein the amplicons from each ROI originate from multiple different individual starting samples. This pooled amplicon sample can be processed as desired by the user (e.g., subjected to sequence analysis, e.g., using next generation sequencing technology).

It is noted here that in certain embodiments, the amplicons produced for each ROI from the circularized and/or immortalized pooled library (e.g., primary amplicons as in FIG. 1A) are already structurally defined. This may be the case when employing restriction enzyme digestion to generate the fragments from the starting polynucleotide samples. In these embodiments, the primary amplicons for a particular ROI can be generated, subjected to QC, and pooled without the intervening steps used to generate the secondary amplicons described above. Furthermore, in such embodiments, a sequencing primer site (e.g., a 454B primer site, where '454B' refers to a sequencing primer used in the Roche/454 sequencing process) may be introduced as a 5' tail on one of the PCR primers so as to produce amplicons which may be sequenced directly (e.g., in the Roche/454 sequencing process).

It is further noted that in some embodiments, structurally variable amplicons may be employed directly for subsequent processing (e.g., sequencing). The decision of whether to process structurally variable amplicons remains with the user, and in general will be based on the particulars of the subsequent process employed. As but one example, the Illumina sequencing platform allows one to select for and analyze amplicons having a desired structure. First, the Illumina process employs an in-situ amplification reaction from a single starting molecule that relies on the relative position of two amplification primer binding sites, thereby forming a "cluster" of multiple copies of the single starting molecule. If the primer binding sites in an amplicon are not in the proper orientation, they will not be amplified, and thus fail to form a cluster that can be sequenced. In addition, the Illumina platform allows for repeated interrogation of the sequence of a single cluster. As such, repeated interrogations can be performed from multiple desired starting points in sequential sequencing runs (e.g., from either end and/or internal starting points). This allows for the sequencing of all or part of a ROI in a first sequencing reaction for a single amplicon molecule followed by sequencing of the MID for that same amplicon molecule in a separate sequencing run. (See, e.g., FIGS. 4C and 4D.)

In certain embodiments, amplicons may be size-selected prior to sequencing to ensure that any amplicons sequenced are of appropriate length for the sequencing platform used.

Exemplary Workflows

Below is provided descriptions of exemplary asymmetric adapters (FIG. 2) and their use in exemplary workflow steps according to aspects of the subject invention (FIG. 3A to 3H). As is noted throughout, the asymmetric adapters of FIG. 2 and the workflow of FIG. 3 are meant to be exemplary and not limiting, as numerous different adapters may be employed in the subject invention and the workflow described below may have steps added, deleted or modified as desired by the user.

FIG. 2 shows exemplary asymmetric adapters that find use in the subject invention. The structures shown in panels A, B, C and D are similar except for the identity of certain adapter domains (described below). An asymmetric adapter includes one or more clamp regions (or inner stem region, ISR) 201, a ligation site 204 and an unpaired region 202/203 (or an overhang on either strand, not shown) such that when an asymmetric adapter is ligated to both ends of a nucleic acid fragment and the adapter-ligated fragment is amplified (or replicated) through the unpaired region, the resultant nucleic acid fragments are tagged asymmetrically, i.e., the nucleic acid fragment(s) produced have at least one different tag sequence, or modified nucleotide/nucleoside, on one end as compared to the tag sequence on the other end. As shown in FIG. 2, each adapter includes two nucleic acid strands—a top strand and a bottom strand—that hybridize to one another to form clamp region 201. When ligated to a compatible end of a nucleic acid fragment via ligation site 204 (which in this case includes a 3'T overhang, although other ligation sites may be used as desired and described above), the clamp region will be proximal to the nucleic acid fragment (also referred to as "inner"). As such, the sequence in the clamp region of the top strand is substantially (or completely) complementary to the sequence in the clamp region of the bottom strand.

Figure 2A:
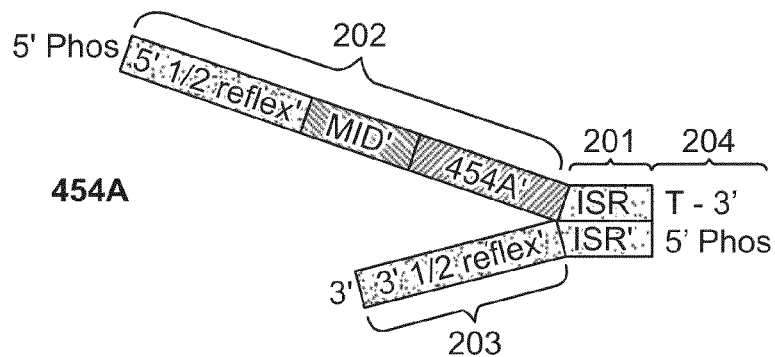
FIGS. 2A, B, C and D show exemplary asymmetric adapters that find use in the subject invention. The structures shown in panels A, B, C and D are similar except for the identity of certain adapter domains (described below).

As indicated in FIG. 2A to D, asymmetric adapters find use in subsequent processing/sequencing in 454 (2A and 2D), Illumina (2B) and SOLiD (2C) sequencing platforms. The adapters include the following domain structures:

FIG. 2A (exemplary 454 adapter for use with the Roche/454 sequencing system): 5' Phos=5' Phosphate; MID=multiplex identifier; ISR=inner stem region (or clamp region); 5' ½ reflex'=5' part of the reverse complement of the reflex site; 3' ½ reflex'=3' part of the reverse complement of the reflex site; 454A=the forward sequencing primer binding site for 454-based sequencing. (Note that the 5' ½ reflex' and 3' ½ reflex' sites will be joined upon circularization to form the full reverse complement of the reflex site, as described below).

Figure 2B:
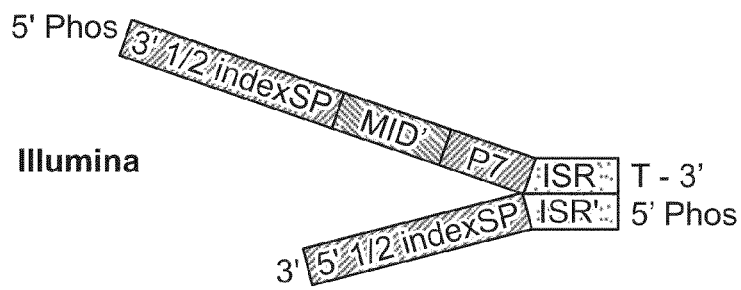
FIG. 2E shows an exemplary workflow for tagging and circularization using the asymmetric adapter of FIG. 2D (combinatorial asymmetric tag).

FIG. 2B (exemplary Illumina Adapter for use with the Illumina sequencing system): 5' Phos=5' Phosphate; MID=multiplex identifier; ISR=inner stem region; 3' ½ indexSP=3' part of the index sequencing primer; 5' ½ indexSP=5' part of the index sequencing primer (circularization forms full indexSP, which is the full-length indexing sequencing primer; the full indexSP may also be used as a reflex site); the reverse complement of indexSP is called Rd2 SP, or the read 2 sequencing primer; P7=flow cell attachment site for bridging amplification in the Illumina sequencing system.

Figure 2C:
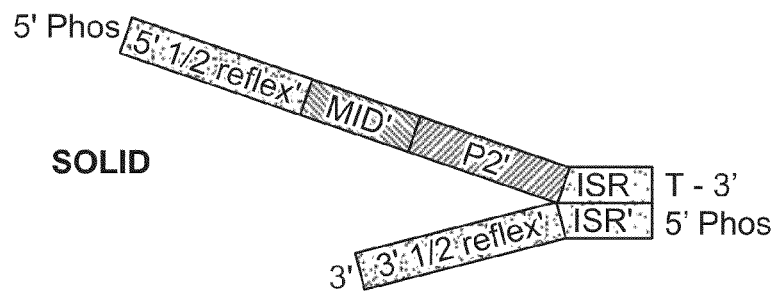

FIG. 2C (exemplary SOLiD Adapter for use with the SOLiD sequencing system from Life Technologies): 5' Phos=5' Phosphate; MID=multiplex identifier; ISR=inner stem region; 5' ½ reflex'=5' part of the reverse complement of the reflex site; 3' ½ reflex'=3' part of the reverse complement of the reflex site; P2 is the sequencing primer that reads the MID sequence. (Note that the 5' ½ reflex' and 3' ½ reflex' sites will be joined upon circularization to form the full reverse complement of the reflex site, as described below).

Figure 2D:
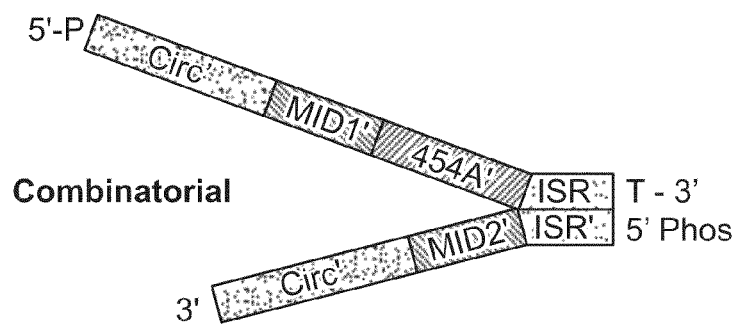

FIG. 2D (exemplary combinatorial adapter): 5'-P=5' phosphate; Circ'=circularization domain complementary to circularization oligonucleotide (e.g., a "splint" oligonucleotide); MID1'=first MID region; MID2'=second MID region; 454A'=the forward sequencing primer binding site for 454-based sequencing; ISR=inner stem region.

Figure 2E:
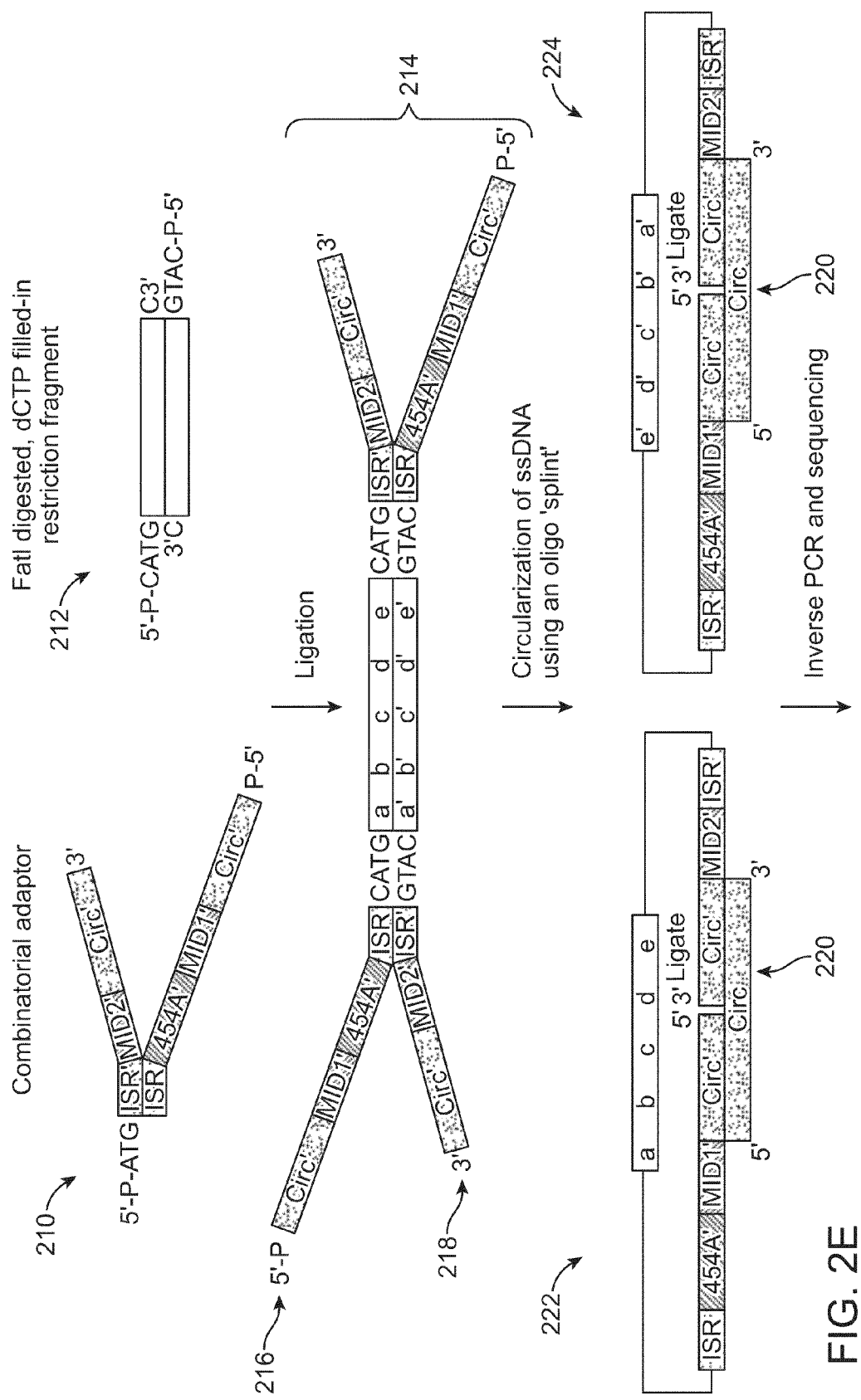

FIG. 2E shows an exemplary workflow of combinatorial tagging using the asymmetric adapter shown in FIG. 2D. Combinatorial asymmetric adapters (210) are ligated to double-stranded polynucleotide fragments (212) having compatible ends to produce adapter-attached products (214). Circularization of the resultant single stranded, asymmetrically-adapted polynucleotides (216 and 218) using the cognate circularization oligonucleotide (220, also called an oligonucleotide "splint") results in circularized products (222 and 224) which can be employed in subsequent steps (e.g., inverse PCR).

The use of combinatorial tagging as exemplified herein would (1) require fewer adapter oligos, and (2) allow the identification of molecules that have undergone inter-molecular ligation and recombination during subsequent processing steps (e.g., circularizing, reflex, etc., as detailed below).

With respect to (1) above, combinatorial adapter can be produced by annealing two oligos, both of which have MID sequences (e.g., MID1' and MID2' as shown in the adapter of FIG. 2D). Different combinations of these oligos can thus generate different asymmetric adapters. For example, 32 'top' and 32 'bottom' strands can give 32×32=1,024 adapter combinations. Thus, rather than having to synthesize 1,025 different oligonucleotides to tag 1,024 different samples (i.e., 1,024 MID containing "top" strands and 1 common "bottom" strand), one would only need to synthesize 64 different oligonucleotides (i.e., the 32 'top' and 32 'bottom' strands noted above). This reduces the number of different oligonucleotides needed by 961 (1,025–64).

An additional benefit of a combinatorial tagging approach is that inter-molecular ligation, which can occur during the circularization process, can be detected. For example, during circularization, the MIDs on the 'top' and 'bottom' strands become juxtaposed such that a read from 454A goes through the 'top' MID and then through the 'bottom' MID (see, e.g., the relative position of domains in circularized polynucleotides 222 and 224 in FIG. 2E). This juxtaposition allows one to read the MID associated with both the 5' and the 3' end of any given strand.

By using an adapter set that has a greater number of different combinations than the number of genomes that are tagged and pooled (i.e., not all MID combinations are employed to identify a starting genomic sample in a pooled sample), one can identify cases when the 'top' and 'bottom' MIDs do not match a known starting genome, thereby identifying instances of undesirable inter-molecular ligation events.

The following equation describes the redundancy needed to identify an MID switch with a given probability. $p=1-(1000/m^2)$ where: p=the probability that an MID switch is detected and m=the number of MIDs (assuming a combinatorial strategy using an equal number of 'top' and 'bottom' strands). Note that m is equivalent to the number of adapters rather than the number of oligos: the required number of oligos is 2 m. Examples are given in Table 1. As an exemplary case, using 142 'top' and 142 'bottom' strand oligos (284 in total) there is a probability of 0.95 that we can detect an inter-molecular ligation event (or a probability of 5% that we would fail to detect an inter-molecular ligation event). Obviously ordering more oligos than the simple case using 32 'top' and 32 'bottom' strands increases cost. However, costs are still less than our current strategy; using 284 oligos would save 716 oligos for 1000 adapters.

We can therefore tune the number of 'top' and 'bottom' strands based on the level of detection of inter-molecular ligation we require. Note that when m=1000, p does not equal 1 because we cannot identify the case where a molecule is inter-molecularly ligated to a second molecule from the same sample.

TABLE 1

| Probability of detecting inter-molecular ligation for different numbers of MIDs. | |
|---|---|
| m | p |
| 32 | 0.02 |
| 50 | 0.60 |
| 100 | 0.90 |
| 142 | 0.95 |
| 250 | 0.98 |
| 500 | 0.996 |
| 1,000 | 0.999 |

It is noted here that subsequent explanations will focus on the use of adapters that find use in the Roche 454 sequencing platform. It will be apparent to one skilled in the art how similar processes can be used if other sequencing platforms are used (e.g., Illumina, SOLiD, etc.). Moreover, the adapters shown in FIGS. 2A to 2D are exemplary and thus, depending on the specific subsequent processes or analyses that are contemplated by the user, adapters having significantly different structural configurations and domains may be used.

Adapters of the present invention can have a wide variety of different domains, and thus can vary significantly in length. In certain embodiments, the oligonucleotides that form adapters as shown in FIG. 2 have a longer top strand of about 60 to 70 nucleotides and a shorter bottom strand of about 20 nucleotides. For example, the longer top oligonucleotide of FIG. 2A may include a 9 nucleotide (nt) inner stem region (ISR), a 30 nt 454A sequence, an 11 nt MID, and a 9 nt 5' ½ reflex' site, and a 1 nt T overhang (60 nt total). The shorter bottom strand may include a 9 nt ISR and a 9 nt 3' ½ reflex' site (18 nt total).

It is further noted that the 5' ½ reflex' and 3' ½ reflex' sites are meant to be merely exemplary and that other functional domains may be produced upon circularization. Thus, these sites are sometimes referred to generically as 5' and 3' ½ Circ domains. For example, in certain embodiments, the 5' ½Circ domain site may include a first half (or portion) of the T7 RNA polymerase site sequence and the 3' ½ Circ domain site may include the second half (or portion) of the T7 RNA polymerase site sequence positioned such that circularization of fragments having these sites at opposite ends will result in formation of the full T7 RNA polymerase site sequence (18 nt in length). It is further noted that the use of "½" in the name of the circularization domains does not mean that each must contain exactly ½ of a functional domain; it is merely meant to indicate that, once joined together, these domains form a larger functional domain or hybridize to the same circularization oligonucleotide (as described below).

Variations to the domains in the asymmetric adapters may be made to prevent certain undesirable side reactions in subsequent process steps (e.g., the generation of undesirable PCR products). For example, consider the simple single DNA strand having reflex sites positioned as follows:

5'-(Primer site A)–(Reflex)–[Insert]–(Reflex')-3'.

Where Reflex' is complementary to the Reflex sequence. After performing a reflex reaction, the following product is generated:

5'-(Primer site A)–Reflex–[Insert]–(Reflex')–(Primer site A')-3'.

This molecule can then be PCR amplified using a single primer specific for the A site. However, in some protocols, this reaction is not a desired product (e.g., when amplifying with an A specific primer and a primer specific for a region in the insert to generate a product having only a single Reflex site). To prevent the generation of a PCR product from two A site specific primers, thereby favoring the generation of the desired product, the domain structure of the single stranded DNA could be designed to have the following structure:

5' (Primer site A)–(Reflex*)–[Insert]–(Reflex')-3'.

The Reflex* sequence is modified such that a base close to the 3' end of Reflex* is replaced by a replication-blocking modification (e.g., a spacer, a bulky dye modification, dUTP, etc.). For example, the incorporation of dUTP will cause a proofreading DNA polymerase to stop opposite (or close to) the dUTP. The reflex reaction can still occur, because the 3' Reflex' and the Reflex* are complementary and because during the extension reaction the polymerase does not have to cross the replication-blocking spacer. The product generated in the reflex (shown below) sequence cannot be PCR amplified using a single primer A because the polymerase cannot extend over the replication-blocking spacer.

5' (Primer site A)–(Reflex*)–[Insert]–(Reflex')–(Primer site A')-3'

Considerations for sites that are useful for circularization of fragments using circularization oligonucleotides include (but are not limited to): (1) lack of secondary structure, particularly with respect to other adapter domains; and (2) melting temperature (Tm) of the circularization (or "splint") oligonucleotide to the circularization sites in the fragments. For example, a Tm ~45° C. can be used in conjunction with Taq DNA ligase (optimal incubation temperature for Taq DNA ligase is at or above 45° C. but it does function at both lower and higher temperatures as described on the New England Biolabs web site).

FIGS. 3A to 3H show the steps for one exemplary workflow according to aspects of the subject invention. The exemplary workflow of FIG. 3 is not intended to be limiting. For example, while FIG. 3 employs 454 sequencing primer sites (454A and 454B; Roche 454 sequencing platform), any convenient sequencing primer site or sites may be employed.

Figure 3B:
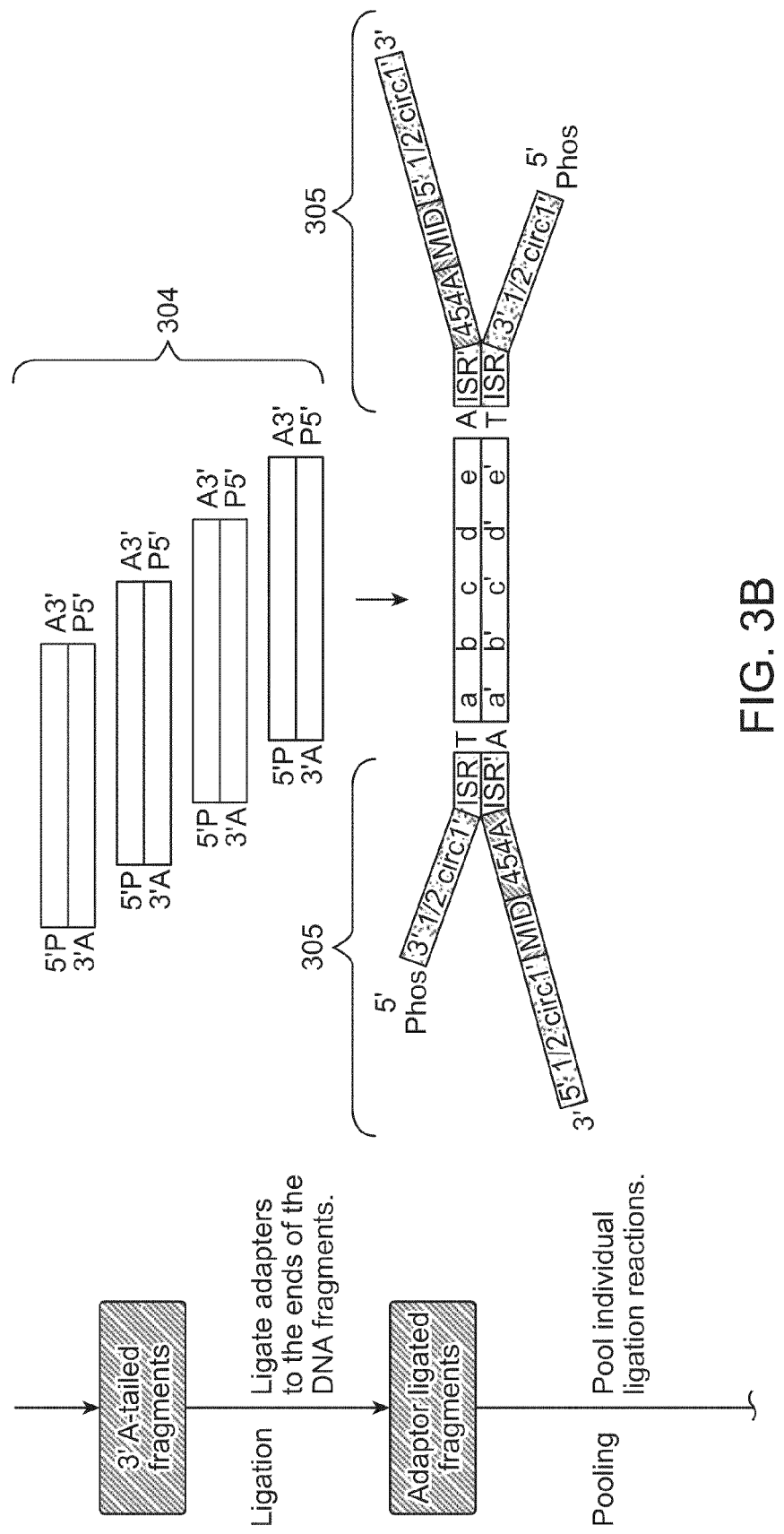
Figure 3B:
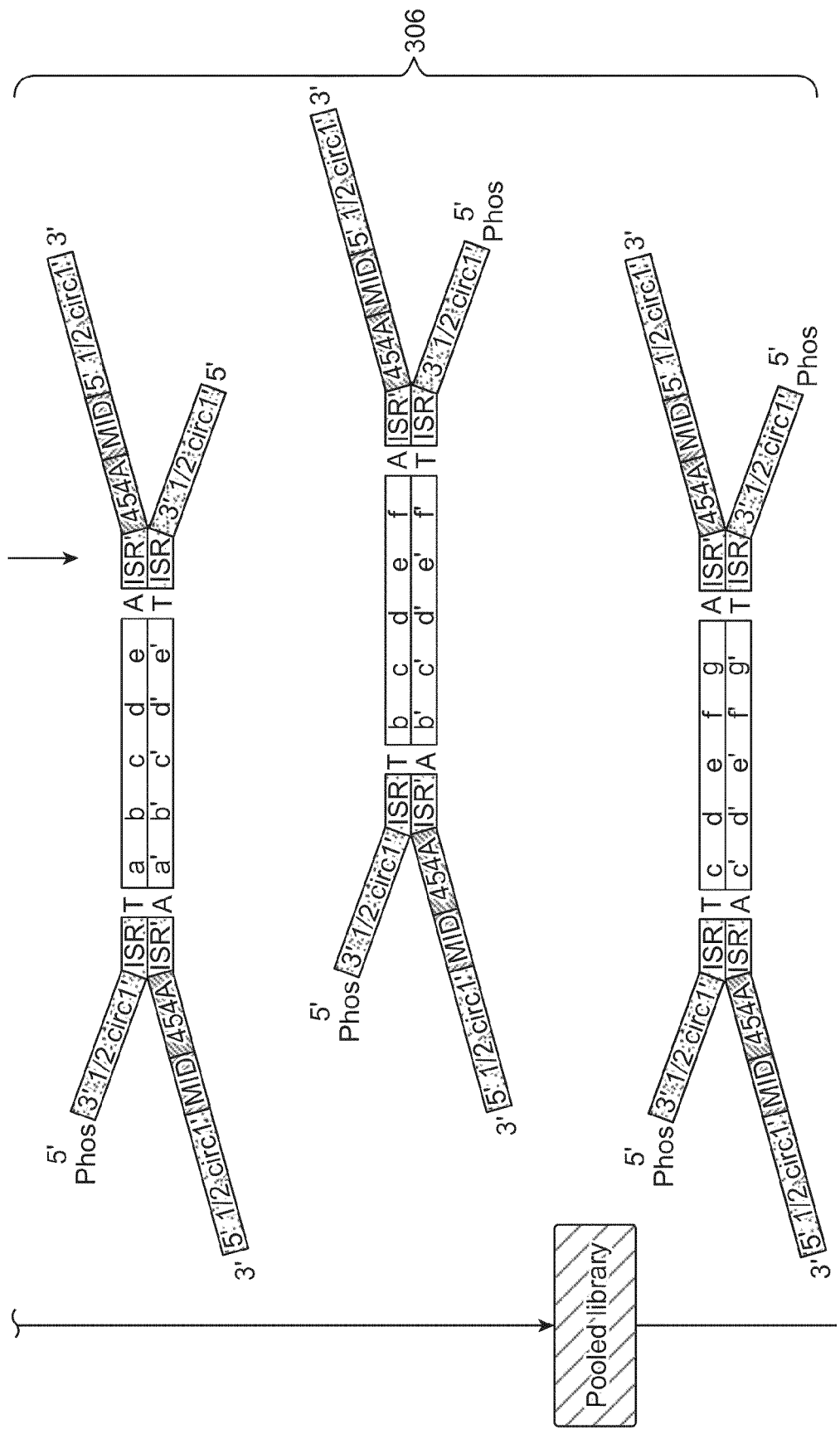

As shown in FIG. 3A, each different sample of genomic DNA 301 is randomly fragmented (e.g., by nebulization, sonication or enzymatic fragmentation) to produce fragments 302. (Note that only one of the multiple samples, each of which actuality is prepared separately, is shown for clarity.) The ends of fragments 302 are made blunt by treatment with T4 polynucleotide kinase, T4 DNA polymerase and/or Klenow enzyme. Polynucleotide kinase can used to remove the 3' phosphate (P) and add 5' phosphates (P) groups. T4 DNA polymerase and Klenow provide both 3'-5' exonuclease activity and polymerase (or 5' "fill-in") activity (shown in 303). Blunt fragments 303 are then A-tailed by treatment with dATP and Klenow fragment lacking 3'-5' exonuclease activity (shown in FIG. 3B, 304).

As shown in FIG. 3B, these A-tailed fragments 304 are then ready for ligation to adapters 305 having a compatible ligation site (e.g., having a 3'T overhang; adapter 305 is shown after attachment to fragments 304). The adapter used in FIG. 3B includes the same domains as the adapter in FIG. 2A except that (i) the 5' and 3' unpaired regions have been switched and (ii) the designation of the circularization domain is changed ("½ circ" in FIG. 3B and "½ reflex" in FIG. 2A). For the sake of simplicity, adapters are shown with only some of the specific domains. Additional domains, such as a degenerate base region, can easily be incorporated as needed (see, e.g., U.S. provisional patent application Ser. No. 61/432,119, filed Jan. 12, 2011; and Casbon et al. Nucl. Acid. Res. 2011, April 13, PMID 21490082, both incorporated herein by reference in their entirety). Note that the adapter used for each different genomic DNA sample includes a sample-specific MID. Thus, once adapters are ligated to fragments from each different sample (and thus tagged with corresponding MIDs), they can be pooled as desired to form a multiplexed sample (306). While the MID domain is denoted in the same manner in each tagged fragment, each MID used to tag the fragments in one sample is distinguishable from every other MID used to tag the fragments in every other sample as employed within a particular pooling experiment. Also note that each fragment shown has a slightly different sequence, i.e., having ROI domains a-e, b-f and c-g; a plurality of different ROI domains would be expected from a randomly fragmented library.

Figure 3C:
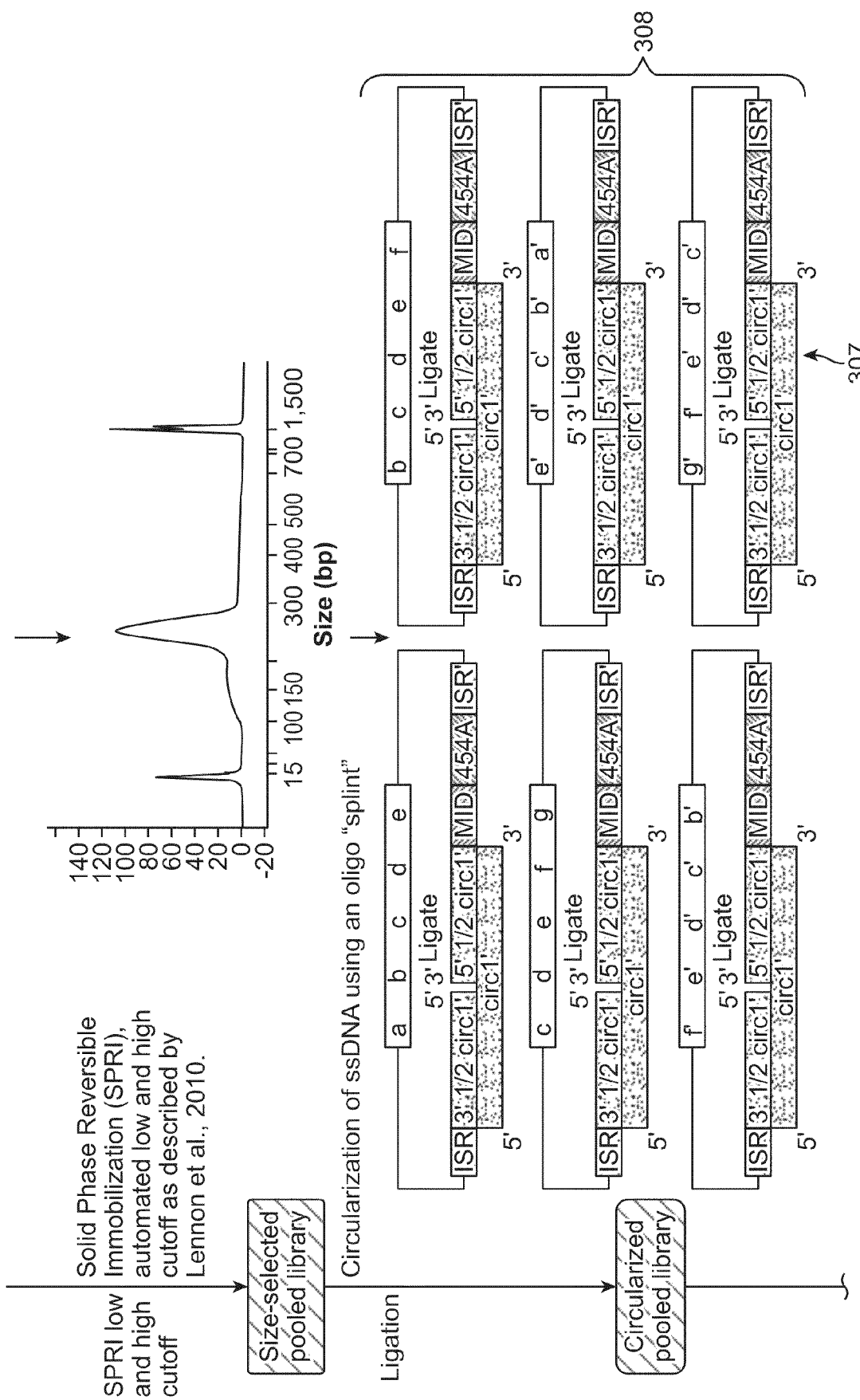
Figure 3C:
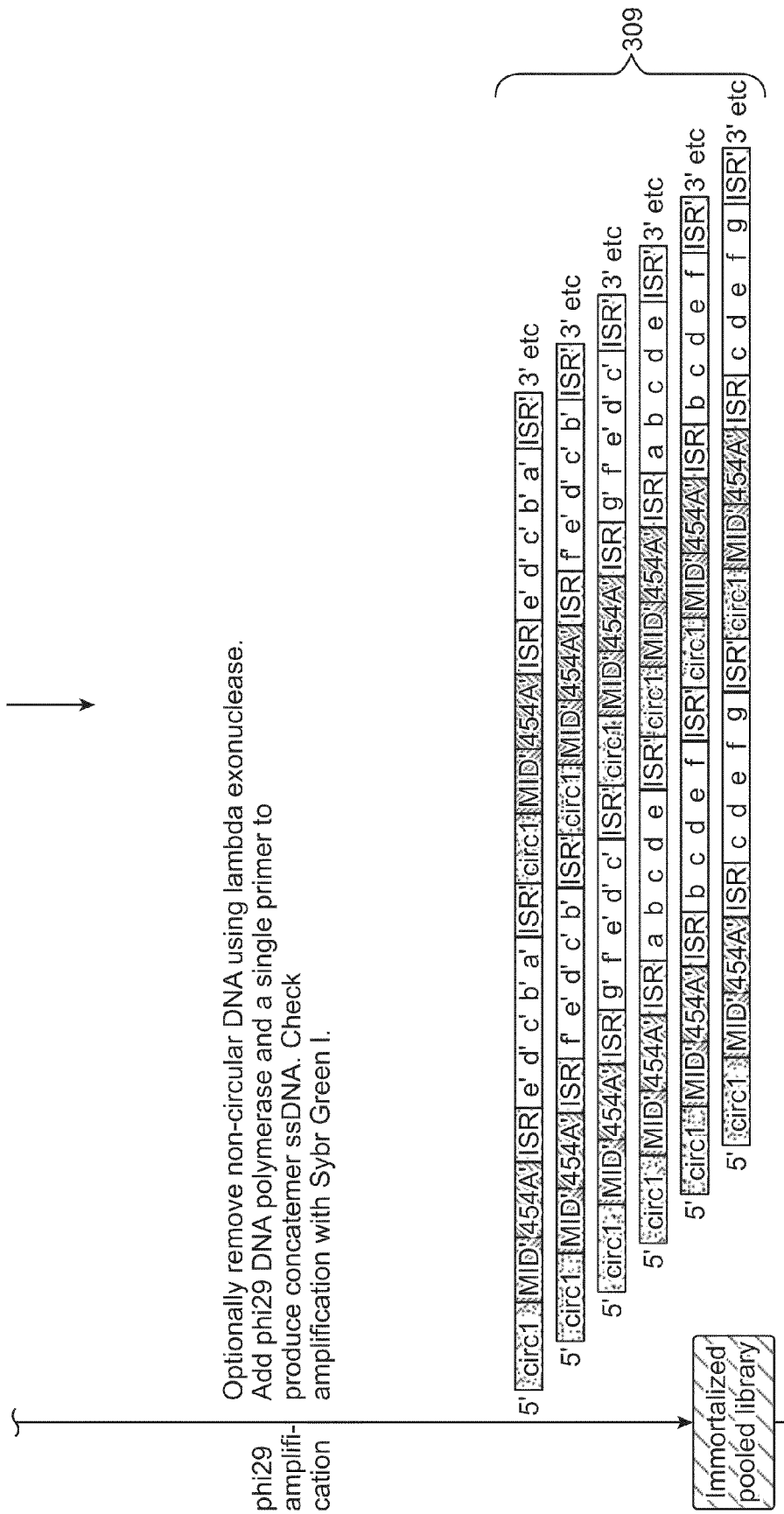

In FIG. 3C, the pooled fragments are size-selected, e.g., using Solid Phase Reverse Immobilization (SPRI) (see, Lennon et al., Genome Biology 2010, v 11, p. R15). Other size selection processes may be employed, as desired by the user. This size-selection process produces a pooled sample that is amenable for manipulation in subsequent process steps, i.e., the sample will not contain adapter ligated fragments that are too short (or free adapters) or too long to be efficiently processed and analyzed. This selection step can be accomplished in any convenient way, and thus no limitation in this regard is intended. In certain embodiments, a size selection step may not be performed. For example, the distribution of randomly fragmented DNA may already be within a specified range.

In certain embodiments, the adapter attached fragments are subjected to a single round of linear amplification (e.g., using a primer specific for a site in the 3' adapter region; not shown in FIG. 3B) to produce asymmetrically tagged polynucleotides (as described in detail above). This single round amplification reaction may be performed prior to combining the adapter tagged polynucleotides into a pooled sample, after the pooling step but before size selection, or after size selection.

After size selection, the adapter tagged fragments are denatured and the ssDNAs are circularized by hybridization to a circularization oligonucleotide 307 (sometimes referred to as a "splint" oligo) and subsequent ligation to produce a circularized pooled library 308. Non circularized DNA, non-hybridized oligos, free adapters, etc., can be removed, e.g., by physical means or by enzymatic treatment, e.g., T7 exonuclease and Exonuclease I (see also Bang et al. "Gene synthesis by circular assembly amplification" 2008 5(1):37-9; incorporated herein by reference). Removal of these excess components can prevent the production of side products in subsequent processing steps. Circularized fragments 308 are then amplified using a single universal primer (i.e., a primer specific for the adapter region) and a DNA polymerase to produce concatamers 309 via rolling circle amplification. In certain embodiments, the DNA polymerase employed has strand displacement activity, where exemplary polymerases include, but are not limited to, phi29, Bst, 9° north, Vent (exo+ and exo−), Deep Vent (exo+ and exo−), Klenow Fragment (3' to 5' exo−), Bsu, Herculase, Pyrophage 3173, Phusion, Therminator, and Sequenase. In certain embodiments, rolling circle amplification is initiated from the hybridized splint oligo 307 used to generate circular DNA in the library preparation step. In embodiments in which phi29 polymerase is employed, the single-stranded DNA concatamer products of the amplification reaction can be long, e.g., 70 kb or more (see, e.g., Blanco et al. (1989) J. Biol. Chem. 264, 8935-8940). Each concatamer is a copy of the original circular molecule and is suitable for direct input into the ROI sequence extraction scheme. Double-stranded DNA can be produced if two primers are used. In certain embodiments, phi29 DNA polymerase-generated concatamers (or concatamers generated using other polymerases) may be fragmented prior to subsequent processing, which can mitigate certain effects of concatenation, including losing representation of individuals in the mixed population. For example, suppose that each circular template from each individual has a mass of 1×. Circular DNA from 100 individuals would thus have a mass of 100×. Amplifying each circular DNA in the sample by 100 fold by making 1 long concatamer of 100 unit lengths from each circle (where 1 "unit length" is the circumference/length of a single circular template prior to the amplification step that produces contcatamers) will result in concatamers each having a mass of 100×, providing a sample of 10,000× total mass, still representing the 100 individuals. If this amplified sample is split into 50 separate tubes, each containing 200× mass of DNA, without first fragmenting the DNA each tube will contain (on average) DNA from only 2 individuals, because each concatamer has a mass of 100×. However, if the concatamers are fragmented into approximately 2 unit length sections prior to splitting into 50 tubes, each tube will contain (on average) DNA from all 100 individuals. This will have achieved a relative amplification fold of 50. It is noted that fragmenting the concatamers to be, on average, >1 unit length will allow for subsequent iPCR amplification, as such fragments would have iPCR primer binding sites in an orientation that allows for the generation of amplicons (see description of iPCR above).

It is noted here that in certain embodiments, extension reactions, other than phi29-based reactions, can be employed to produce immortalized libraries. Such reactions may be performed before or after pooling of the adapter-tagged fragments.

As noted in FIG. 3C, this multiplexed pool of concatamers is sometimes called an "immortalized pooled library". As noted above, immortalization refers to a sample or library that can be used to generate sufficient template polynucleotides (e.g., DNA) repeatedly, i.e., without consuming the sample. Rolling circle amplification using phi29 DNA polymerase may be desirable in certain embodiments because: (1) if a single primer is used, the products of amplification are not themselves amplified, as in PCR, which helps reduce error, (2) phi29 DNA polymerase is active on a variety of sequences, including those with repeats and secondary structures, (3) phi29 DNA polymerase will produce fragments that are on average 70 kb, which equates to 100-fold amplification of a 700 nt adapter tagged fragment, and (4) it is unlikely that MID switching will occur during amplification (i.e., transfer of an MID from one fragment to another). MID switching can be caused by an incomplete extension product from one cycle of a PCR annealing to a non-fully complementary template in either the same or a subsequent PCR cycle. This effect is also called PCR recombination (see, e.g., Meyerhans et al., (1990) DNA recombination during PCR, NAR, 18(7): 1687-91).

It is noted here that MID switching (e.g., due to PCR recombination) can be reduced by specific PCR methodologies. For example, one can use emulsion PCR technology (emPCR; see, e.g., Williams et al (2006) Amplification of complex gene libraries by emulsion PCR, Nature methods 3 (7): 545-550); microdroplet-based technologies (e.g., from RainDance Technologies); or solid phase bridge PCR (e.g., as described in Fedurco, M., Romieu, A., Williams, S., Lawrence, I., and Turcatti, G. (2006). BTA, a novel reagent for DNA attachment on glass and efficient generation of solid-phase amplified DNA colonies. Nucleic Acids Res. 34:e22). Any of these approaches as well as careful alteration of PCR conditions may improve MID representation in the resultant amplicon samples and can be implemented as desired by the user.

Figure 3D:
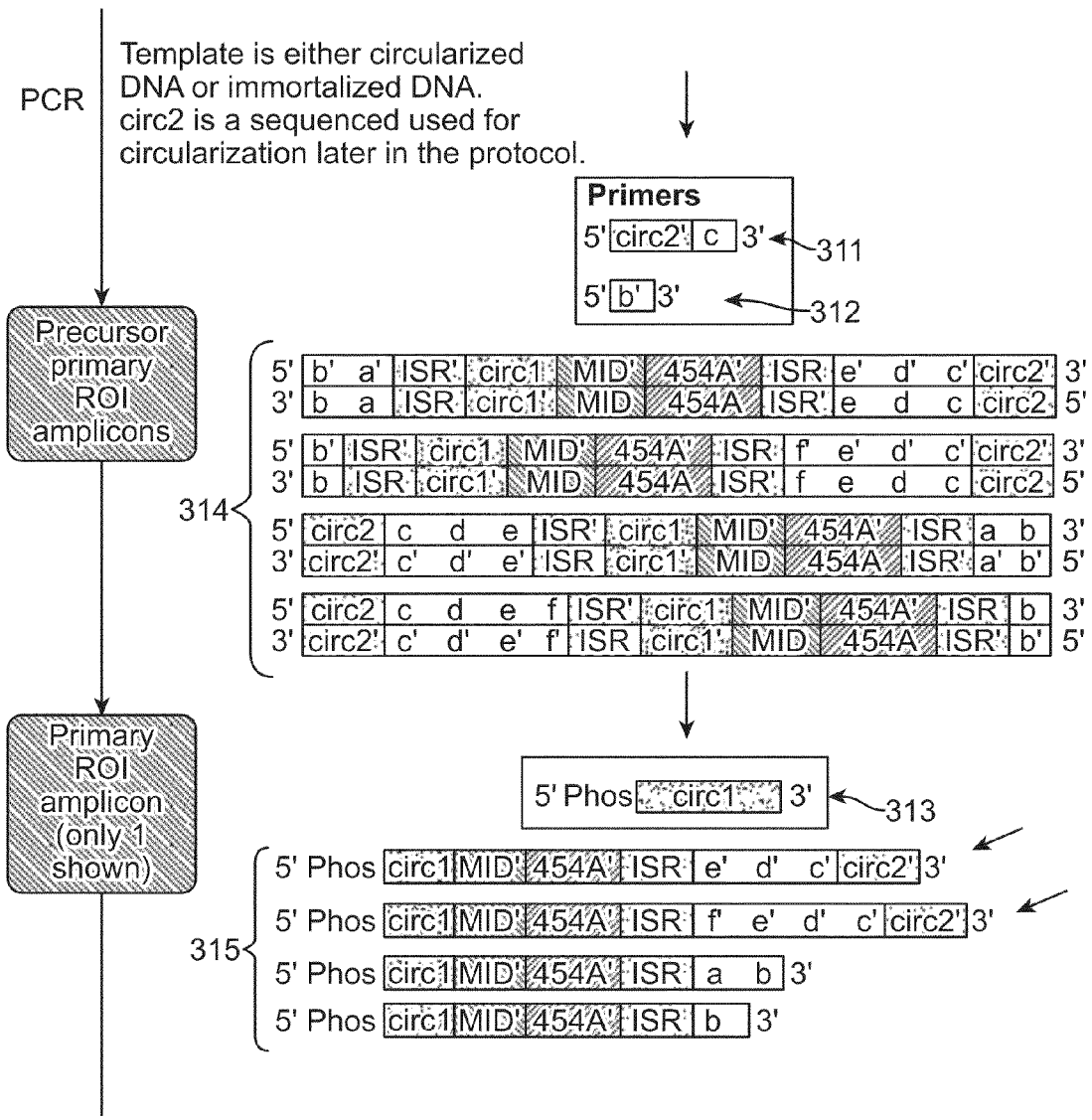
Figure 3E:
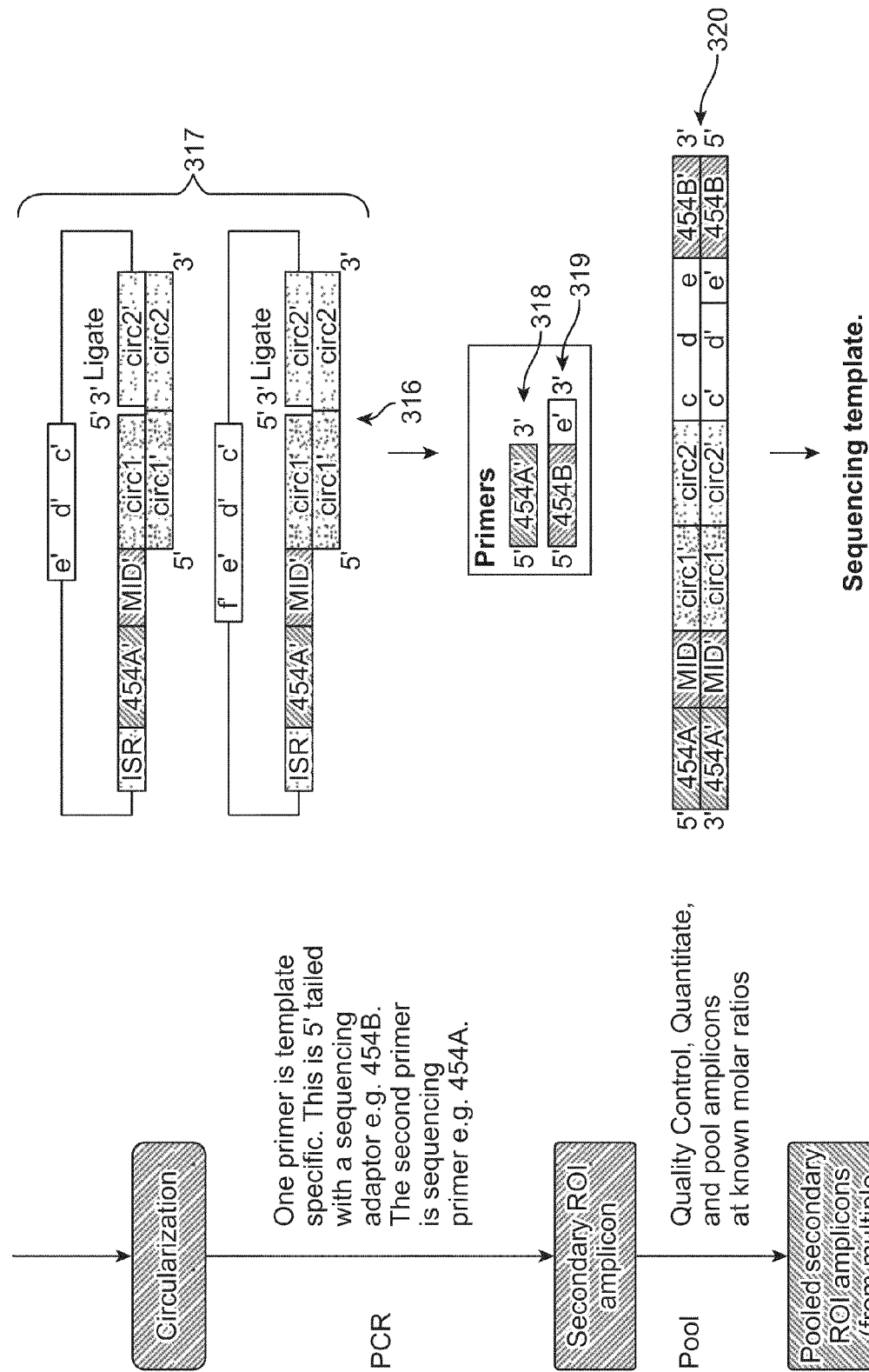

FIGS. 3D and 3E show exemplary steps for the workflow designated 101 shown in FIG. 1B. In FIG. 3D, immortalized pooled library 309 (from FIG. 3C) is subjected to a PCR reaction to produce precursor primary ROI amplicons 314 (the first step in the ROI extraction process). The two primers employed extend through the "c" region of the fragments (primers 311 and 312). Note that these primers are designed to produce precursor primary amplicons that include the ROI as well as adapter domain sequences. This reaction is highly specific, since two independent primers that are specific for two different fragment sequences are used (i.e., neither of the primers are specific for common adapter sequences). In certain embodiments, more than one primer pair may be employed in this PCR reaction as desired by a user (e.g., a multiplex PCR reaction), where each primer pair is specific for a different ROI. In certain other embodiments, the primers used for PCR could be partially overlapping.

In certain embodiments, the PCR reaction is performed directly on the circularized pooled library 308, i.e., without amplification with phi29 polymerase (also called an inverse PCR reaction).

Moreover, it is noted here that when primary ROI amplicons are generated from a restriction enzyme-fragmented library (not shown) instead of randomly-fragmented library, PCR primers can be designed to produce structurally defined primary ROI amplicons directly. A restriction enzyme-fragmented library takes advantage of the fact that the adapter ligation site adjacent to the ROI of interest will be known. This obviates the need for the steps described below for generating structurally defined secondary ROI amplicons from structurally variable primary ROI amplicons.

As shown in FIG. 3D, primer 311 is 5' tailed with a second circularization site (circ2). As its name implies, this second circularization site will be used as a site for hybridization of a circularization oligonucleotide in subsequent process steps. To generate primary ROI amplicons suitable for circularization, precursor primary ROI amplicons 314 are subjected to a primer extension reaction with a primer 313 that hybridizes within the circ1' region and is 5' phosphorylated (to allow subsequent circularization). The resultant circ1 primer extension products 315 (i.e., the primary ROI amplicons) include amplicons, indicated with the arrows, having terminal sequences of circ1 (or a portion thereof) and circ 2'. In FIG. 3E, these circ1/circ2' containing primary ROI amplicons 315 are circularized using circularization oligonucleotide 316, which brings the 5' phosphorylated end and the 3' hydroxylated end of these fragments into proximity to facilitate ligation (see description of circularization above). It is noted that in certain embodiments, enzymatic phosphorylation can be used to generate the 5' phosphorylated end rather than using a 5' phosphorylated primer 313. This circularization reaction produces circularization primary ROI amplicons 317 (shown in FIG. 3E).

In FIG. 3E, circularized primary ROI amplicons 317 are subjected to an amplification reaction using primer 318, which primes in the sequencing primer binding site 454A of the adapter, and primer 319, which primes in the "e" region of the fragments and includes a tail containing the 454B sequencing primer binding site. This reaction produces secondary ROI amplicons 320, which include the desired ROI of "c-d-e" (including any variants/mutants of this ROI in the pooled sample) and the corresponding MID, both of which are flanked by the 454A and 454B sequencing primer binding sites. This secondary ROI amplicon can be used in any subsequent processing/analysis steps as desired by the user.

In certain embodiments, and as shown in FIG. 3E, the secondary ROI amplicons 320 are quantitated and pooled at known molar ratios with secondary ROI amplicons generated for other ROIs as desired. Each different secondary ROI amplicon may also be run through additional quality control processes (QC) prior to pooling and subsequent analysis. In certain embodiments, these pooled secondary amplicons can be subjected to sequencing reactions (in this case using the Roche 454 sequencing platform), or used in additional subsequent processes as desired by the user, e.g., submitted to a process that selects for fragments having a sequence variation within the ROI as compared to a wildtype sequence for the ROI (also called a culling process).

Figure 3F:
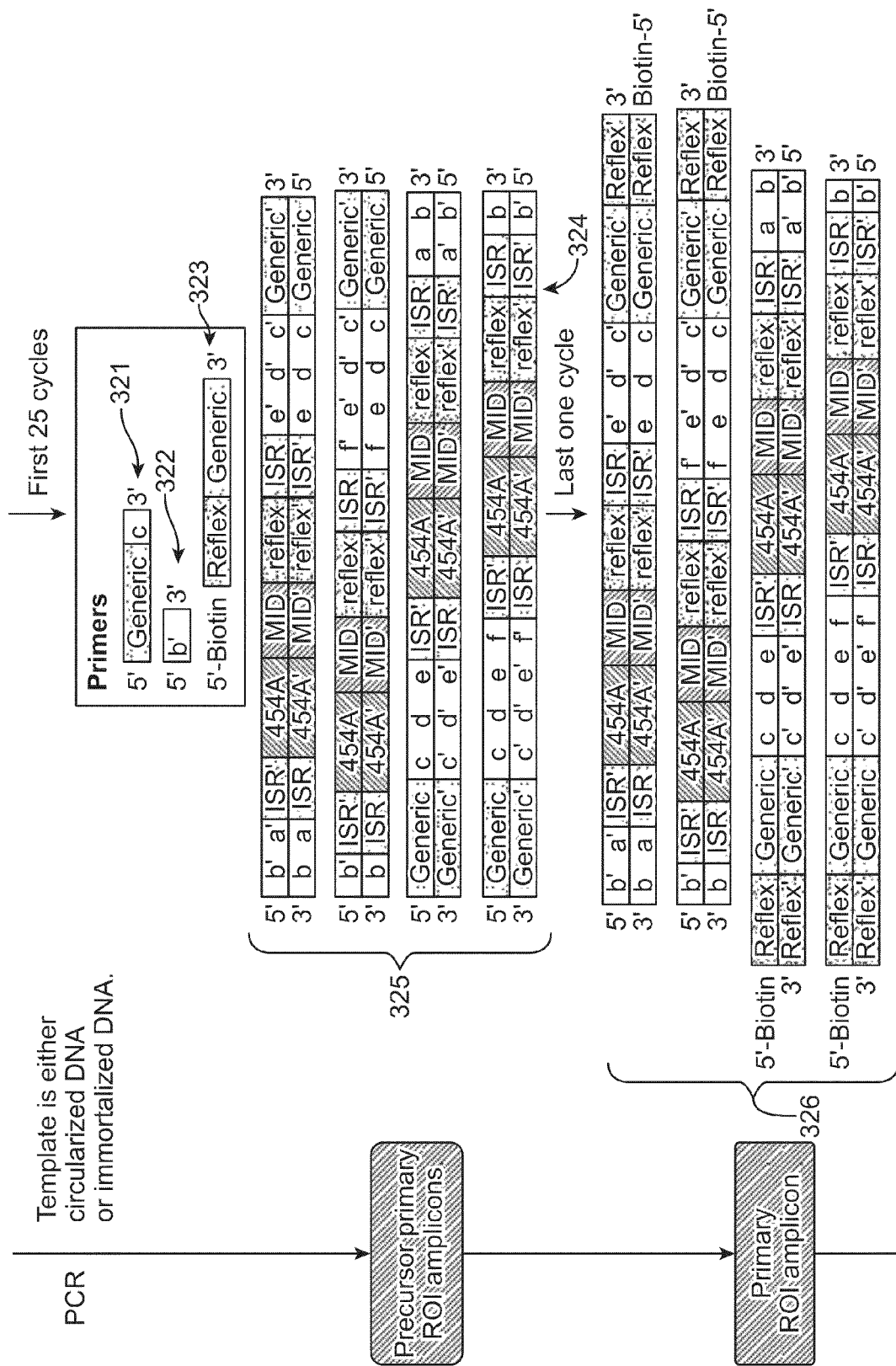
Figure 3G:
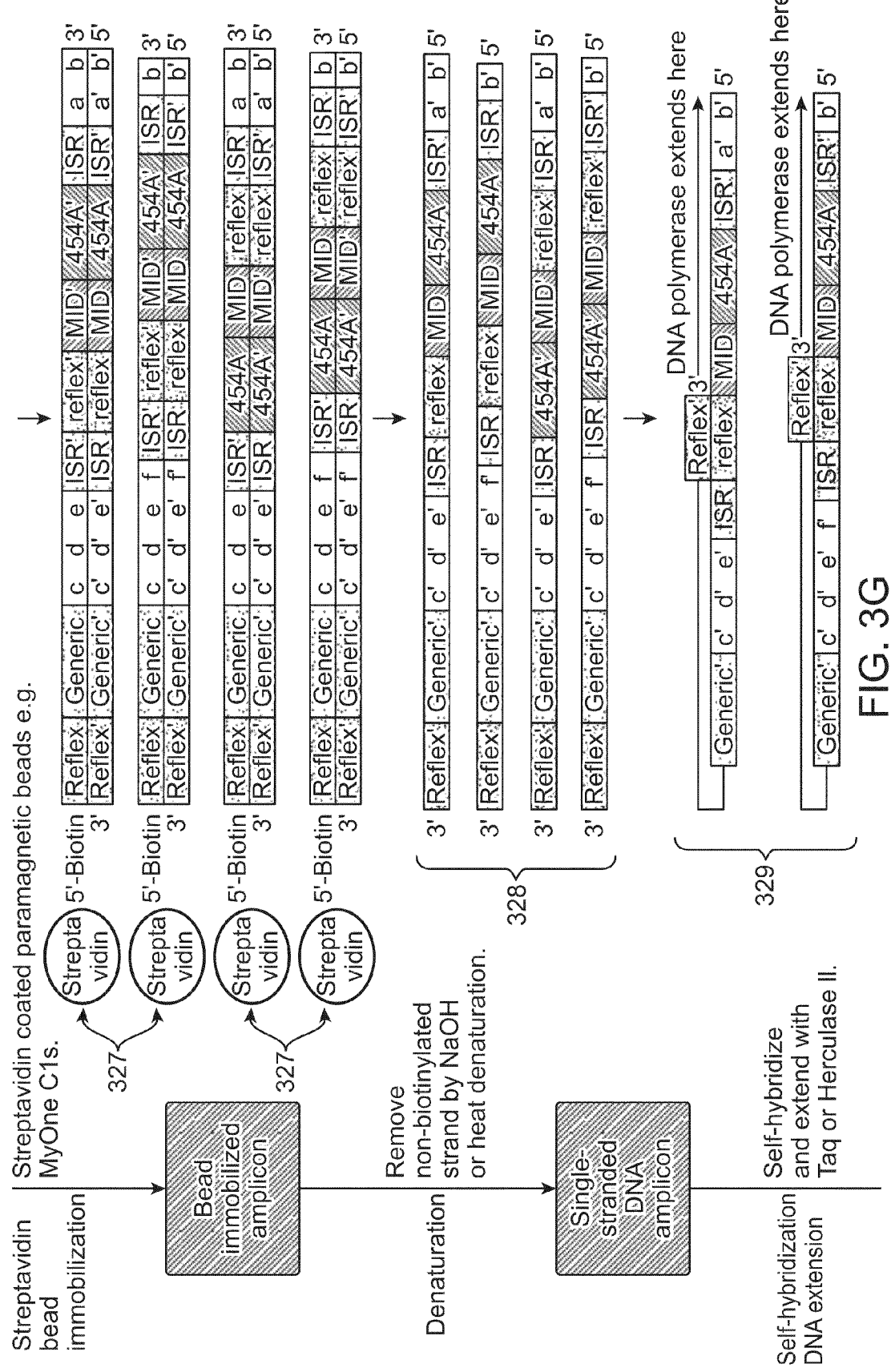
Figure 3H:
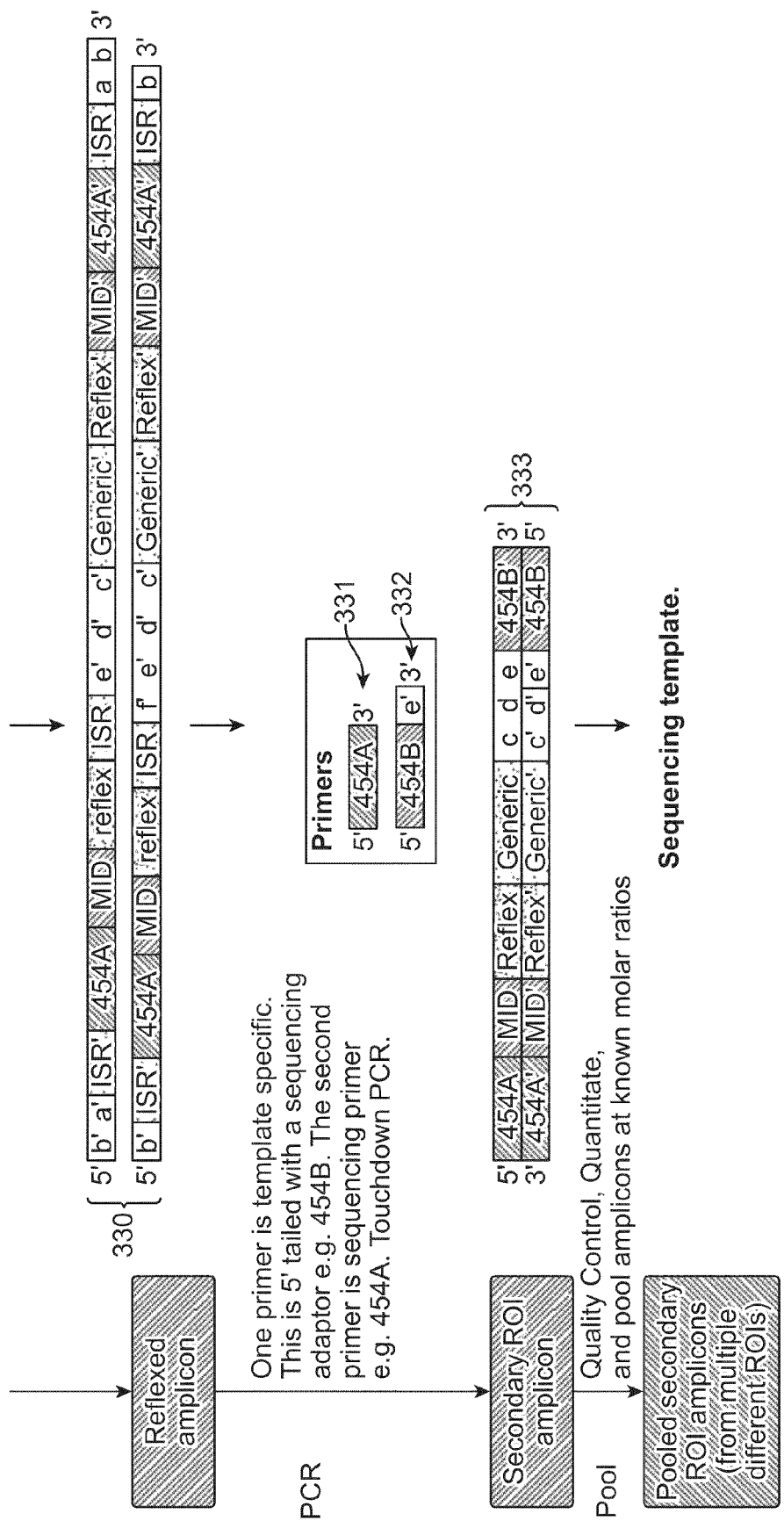

FIGS. 3F to 3H show exemplary process steps as described in workflow steps 102 of FIG. 1B. It is noted that in the amplicons shown in these figures, the adapters used to tag the initial randomly fragmented DNA are identical to that shown in FIG. 2A. Thus, when circularized, the 5' ½ reflex and 3' ½ reflex domains of the adapter are joined to form a reflex site 324 that is employed in the reflex process.

In FIG. 3F, immortalized pooled library 309 (shown in FIG. 3C) is subjected to a PCR reaction to produce primary ROI amplicons (similar to the PCR amplification described for FIG. 3D). In FIG. 3F, two primers that extend through the "c" region of the fragments are used (primers 321 and 322). As in the 101 workflow described above, primers 321 and 322 are designed to produce precursor primary amplicons that include the ROI as well as adapter domain sequences. This reaction is highly specific, since two independent primers that are specific for two different fragment sequences are used (i.e., neither of the primers are specific for common adapter sequences).

The first cycles of the inverse PCR reaction (which includes primers 321 and 322) produces precursor ROI amplicons 325. As shown in FIG. 3F, primer 321 is 5' tailed with a generic priming site. This generic site allows the inclusion of a third primer 323 (which has a sequence specific for the generic sequence; a reflex site; and is 5' biotinylated) in the last cycle to produce primary ROI amplicons 326. Primer 323 is used only in the last cycle of the PCR reaction to prevent undesirable side product generation that may occur if the reflex sequence were placed on primer 321 or 322 (owing to the generation of a reverse complement reflex sequence at the 3' end of the PCR product).

As shown in FIG. 3F, primary ROI amplicons 326 have one biotinylated strand and two reflex sites, one complementary to the other (as needed to perform a reflex reaction). It is noted here that primer 323 may be used in the last cycle of any primary ROI specific amplification reaction (e.g., the PCR amplification shown in FIG. 3F) in which one primer includes the generic tail sequence (e.g., as does primer 321). Thus, if a user is amplifying a plurality of different ROIs in a plurality of different primary ROI amplification reactions, and one primer in each reaction includes the same generic tail sequence, the same biotinylated primer may be used in the last step of all of the primary ROI amplification reactions. However, a user may decide to use different generic tail sequences for each different primary ROI amplification reaction (or a subset thereof), thus requiring the use of multiple different generic tail-specific primers for the last cycle of the primary ROI PCR reaction.

It is noted again here that if primary ROI amplicons are generated from a restriction enzyme-fragmented library (not shown), primers can be designed to produce structurally defined primary ROI amplicons, as the adapter ligation site adjacent to the ROI will be known. This obviates the need for the steps described below for generating structurally defined secondary ROI amplicons from the primary ROI amplicons 326. In addition, and as noted above, these primary amplicons can be normalized and pooled directly (e.g., by subjecting them to one or more desired QC analysis).

When random fragments are processed, the primary ROI amplicons are structurally variable (326, as shown in FIG. 3F), corresponding to the original size range of the library fragments that contain the ROI (in this case, region "c"). To generate secondary ROI amplicons from the primary ROI amplicons, a reflex reaction is first performed. The reflex process is described in PCT application IB2010/002243, filed on Aug. 13, 2010 (published as WO 2011/021102), and entitled "Compositions and Methods for Intramolecular Nucleic Acid Rearrangement Using Reflex Sequences", incorporated herein by reference. The reflex process can be employed to produce structurally defined secondary ROI amplicons that are useful for subsequent processing (e.g., that can be normalized prior to sequencing, as described below).

It is noted here that the products from the multiple primary/secondary ROI amplification reactions may be obtained using the same type of amplification reaction or from different types of amplification reactions. For example, amplicons for a first ROI may be produced by standard PCR reactions whereas amplicons for a second ROI may be obtained using a reflex reaction. No limitation in this regard is intended.

In the embodiment shown in FIGS. 3F to 3H, single-stranded DNA is first isolated to use in the reflex process. However, it is noted here that isolation of single-stranded DNA is not necessary to perform the reflex reaction, and thus in certain embodiments this step is not done. In FIG. 3G, isolation of single-stranded DNA is achieved by binding the primary ROI amplicons 326 to a streptavidinated solid support (streptavidin beads 327) via the biotin moiety. The non-biotinylated strand is then denatured from the biotinylated strand, eluted (isolated) 328, and input into a reflex reaction (329). In the reflex reaction, the reflex site and its complement in each polynucleotide strand are allowed to hybridize intramolecularly and are then extended (e.g., using DNA polymerase) to generate reflexed products 330 (shown in FIG. 3H). Any convenient methods for isolation of single-stranded DNA may be employed, e.g., protecting one strand from exonuclease digestion (e.g., by including a phosphorothioate linkage(s) into the 5' region of primer 321) followed by exonuclease treatment (e.g., T7 or lambda exonuclease).

Regardless of whether single-stranded DNA is isolated or not, the amplification primers (e.g., PCR primers) should be removed from the variable length amplicons as they can interfere with the reflex process. Any convenient method to remove the primers may be employed, including enzymatic (e.g., ExoSAPit) or physical (e.g., Agencourt SPRI beads) processes.

In certain other embodiments, it is the biotinylated strand that is isolated rather than the non-biotinylated strand. Once the non-biotinylated strand is eluted/washed away, the biotinylated strand may be removed from the substrate and isolated. For example, in embodiments in which the biotin moiety is attached to the DNA strand via a cleavable linker, the substrate-bound DNA can treated with an agent that cleaves the cleavage site of the cleavable linker to isolate the single stranded DNA. Any convenient single strand DNA isolation technique may be used, and as such, no limitation in this regard is intended.

As shown in FIGS. 3G and 3H, the reflex reaction places specific adapter domains of the fragments (e.g., the MID and 454A primer site) into proximity with the ROI domain (domain "c"). This ensures that all ROI-containing amplicons are suitable targets for subsequent amplification to produce the secondary ROI amplicons in subsequent steps. As shown in FIG. 3H, reflex reaction products 330 are subjected to a PCR using 454A primer 331 and a sequence specific primer tailed with 454B site 332. This PCR generates secondary amplicons 333 that have a structurally defined insert sequence (i.e., c-e; excluding genetic variants) and adapter sequences (454 A and B sites, MID, Reflex and the generic tail sequence). This secondary ROI amplicon can be used in any subsequent processing/analysis steps as desired by the user.

In certain embodiments, and as shown in FIG. 3H, secondary ROI amplicons 333 are quantitated and pooled at known molar rations with secondary amplicons generated from other ROIs as desired. Each different secondary amplicon may also be run through additional quality control processes (QC) prior to pooling and subsequent analysis. In certain embodiments, these pooled secondary amplicons can be subjected to sequencing reactions (in this case using the Roche 454 sequencing platform), or used in additional subsequent processes as desired by the user, e.g., submitted to a process that selects for amplicons having a sequence variation within the ROI as compared to a wildtype sequence for the ROI (also called a culling process).

In certain embodiments, the secondary ROI amplicons (e.g., produced by the methods described above), either prior to or after pooling, are subjected to a "generic" amplification reaction prior to subsequent steps/analysis. By "generic amplification" reaction is meant that the amplification reaction is designed not to be specific for a specific ROI. For example, the secondary ROI amplicons 323 can be subjected to a linear or PCR amplification that employs a primer or primer pair that anneals in the common adapter regions. For example, a PCR reaction can be performed that employs a forward primer that hybridizes to all or part of the 454A sequencing primer binding site and a reverse primer that hybridizes to all or part of the 454B sequencing primer binding site. The specific constituents and/or primer/primer pairs employed in this amplification reaction will depend on the desires of the user and the sequences present in the secondary ROI amplicons (e.g., primer binding sites present in the adapter regions). Any suitable amplification reaction may be employed, e.g., linear, non-linear, exponential, etc.

Exemplary Circularization and Inverse PCR Strategies

While the foregoing description exemplified aspects of the subject invention, it is noted that any number of different strategies for implementation are possible. Several different non-limiting examples of variations are provided in FIG. 4.

FIGS. 4A to 4D show 4 exemplary embodiments, or Read Strategies, each having distinct adapter, circularization structure, and amplicon structures. Under "Genomic positions", the relative position and nucleic acid synthesis direction (i.e., 5' to 3') of the inverse PCR (iPCR) primers at the target genomic region (solid arrows) and the sequencing direction and relative starting position of the sequencing primers with respect to the iPCR primers (dotted arrows).

In all cases shown in FIGS. 4A to 4D, these strategies permit 'direct' sequencing of the primary ROI amplicons (structurally variable) from a randomly sheared library, i.e. subsequent reflex or secondary circularization reactions are not required (see description above of using the Illumina sequencing platform with structurally variable amplicons).

The Paired end read+index read strategy (FIG. 4A) employs three distinct reads of a clonally amplified template. The paired end reads (×2) start from defined chosen genomic locations by virtue of tailing the sequencing primers (P5 and P7) to the 5' end of both of the inverse PCR primers used in the enrichment (Rd1SP and Rd2SP). This permits freedom in primer design to start reads from chosen positions on a randomly sheared template library. The third read originates from ligated adapter sequences ('index'), and enables the sequence determination of the MID/DBR associated with the paired end reads (where MID/DBR is an adapter domain that has both an MID and a DBR, both of which are described in detail above). As templates are sheared randomly, the adapter sequence may be captured from one of the paired end reads. This will depend on the probability of such an event, which is governed by circular size and read length parameters. In this case, larger circles will reduce the probability of reading adapter sequence from the paired end reads. To reduce primer costs, common sequences can be added by generic splicing by overlap extension (SOE) to all amplicons.

Figure 4A:
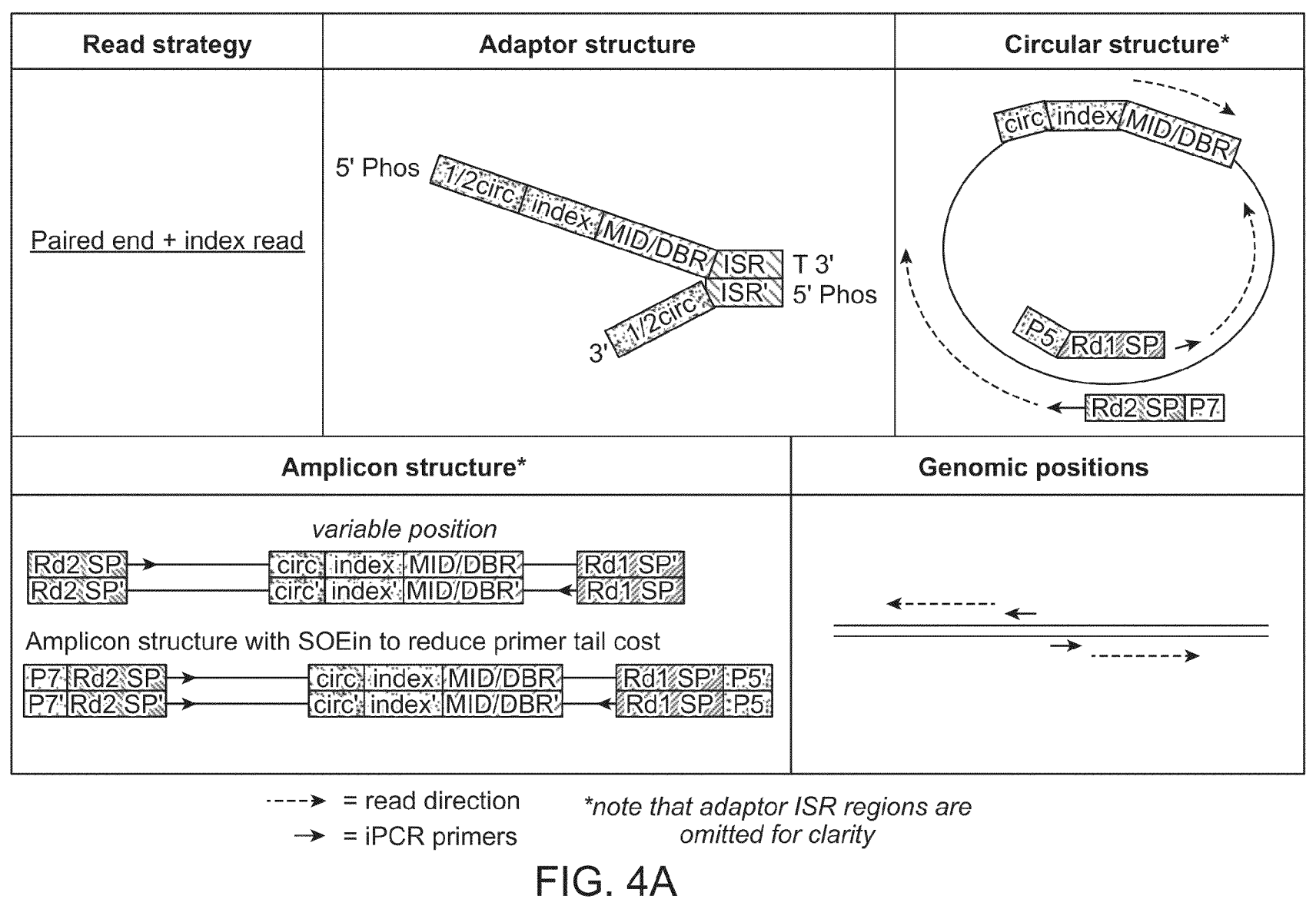
Figure 4B:
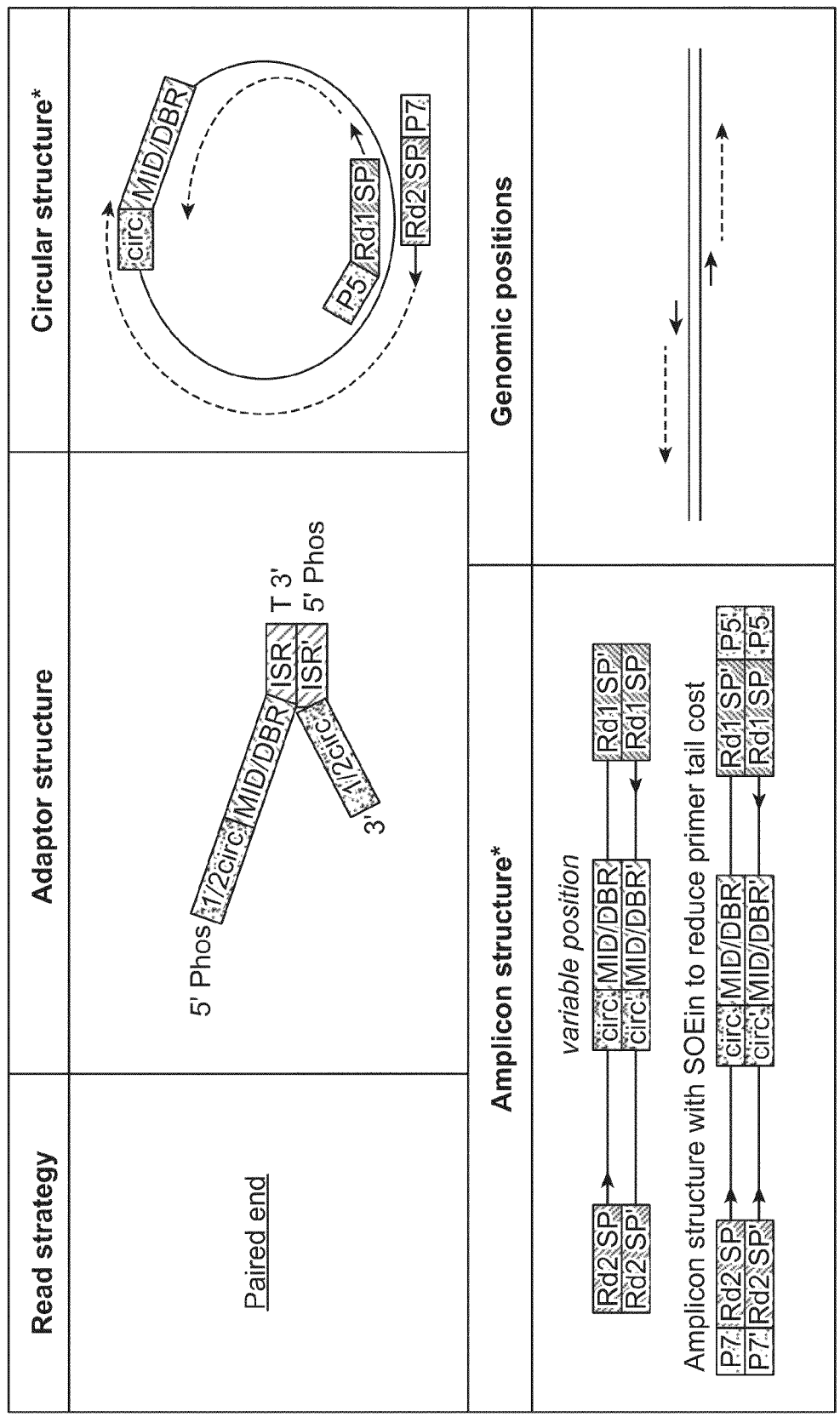
Figure 4C:
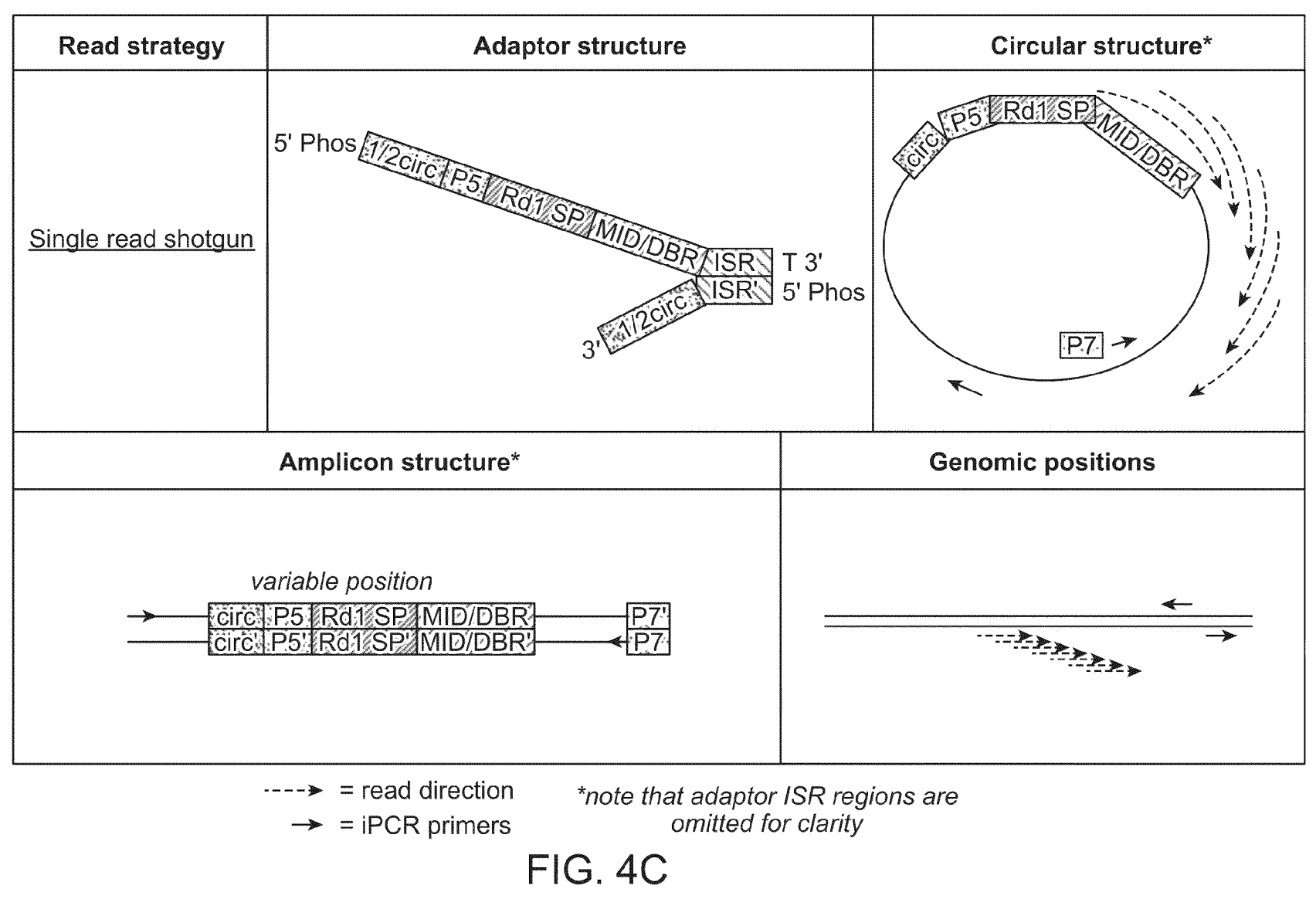
Figure 4D:
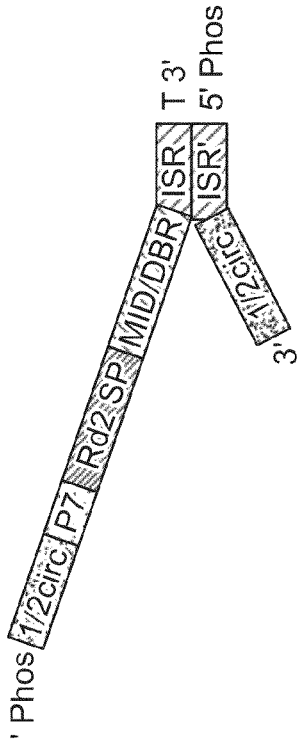
Figure 5:
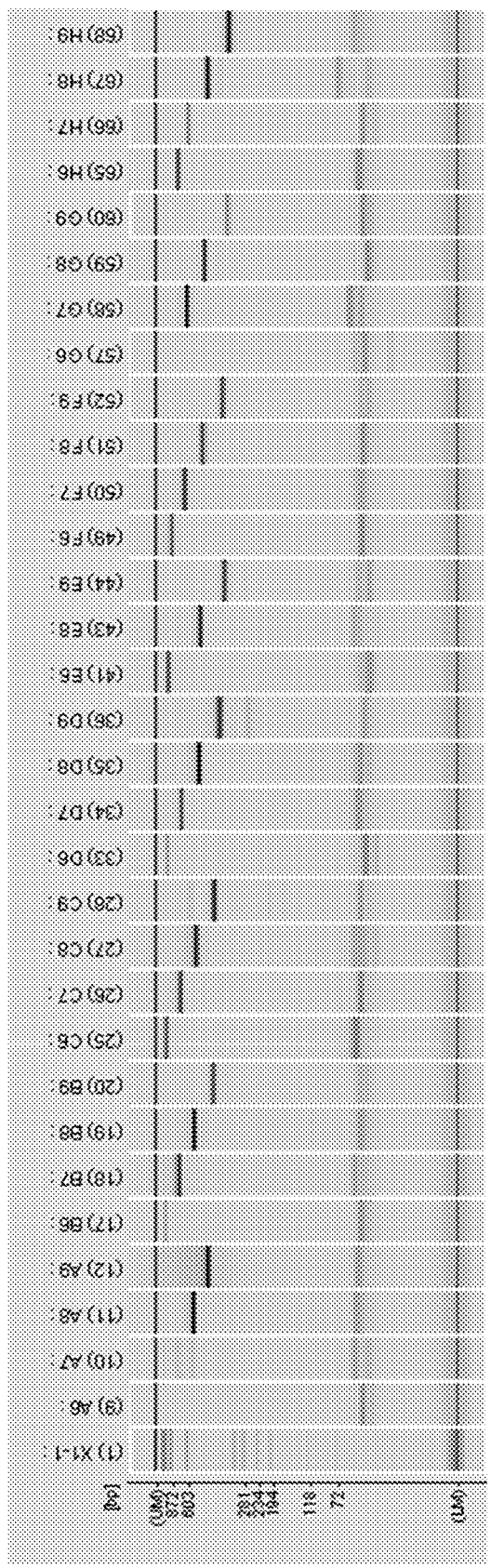
FIG. 5 shows capillary electrophoretic analysis of 38 PCR amplicons generated from a FatI library of genomic fragments (see Example I).

The paired end strategy (FIG. 4B) employs two distinct reads of a clonally amplified template (from the P5 a P7 sequencing primers, as in FIG. 4A). Circular templates are designed to be small enough so that one of the two paired end reads are able to capture the adapter sequences and determine the MID/DBR for each clonally amplified template. This is achieved by using circular DNAs small enough to ensure a high degree of captured MID/DBRs, but not too small as to only capture adapter sequence. As in FIG. 4A, 5' SOE primer tailing can reduce primer synthesis costs.

The single read shotgun strategy (FIG. 4C) employs a random read start position by virtue of the randomly sheared library production. Only a single read is required from each clonally amplified template. Inverse PCR primers (dark arrows, one with P7 tail) are used to specify the locality of the genomic regions to be sequenced, although read start positions are from adapter sequences (P5 site) ligated to adjacent base positions due to random shearing. Each read will capture the MID/DBR, and some genomic sequence in the locality of the inverse PCR primer position. Each inverse PCR reaction will generate multiple read start positions in the population. Consensus sequences for each individual can be built using multiple reads.

The paired end for MID strategy (FIG. 4D) is similar to that of the paired end strategy (FIG. 4B) although genomic sequence is only captured from one of the paired end reads. The second paired end read permits capture of the MID. This strategy may be employed where next generation sequencing permits only two reads, or where genomic targets are small enough to be captured in a single read.

It is noted that in certain embodiments, variable length primary ROI amplicons can be quantified by mass, e.g., using PicoGreen, and combined with other primary ROI amplicons on an equimass, rather than equimolar, basis.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Thus, all combinations of the embodiments pertaining to genetic analysis as disclosed herein (e.g., for polynucleotide library production, immortalization, and region of interest/amplicon production) are specifically embraced by the present invention and are disclosed herein just as if each and every combination was individually and explicitly disclosed.

Kits and Systems

Also provided by the subject invention are kits and systems for practicing the subject methods, as described above, such components configured to add adapter domains or sequences to nucleic acids of interest and reagents for performing any steps in the ROI extraction and/or normalization processes described herein (e.g., adapters, restriction enzymes, nucleotides, polymerases, primers, exonucleases, etc.). The various components of the kits may be present in separate containers or certain compatible components may be precombined into a single container, as desired.

The subject systems and kits may also include one or more other reagents for preparing or processing polynucleotides according to the subject methods. The reagents may include one or more matrices, solvents, sample preparation reagents, buffers, desalting reagents, enzymatic reagents, denaturing reagents, where calibration standards such as positive and negative controls may be provided as well. As such, the kits may include one or more containers such as vials or bottles, with each container containing a separate component for carrying out a sample processing or preparing step and/or for carrying out one or more steps for producing primary and secondary ROI amplicons and/or pools of amplicons according to the present invention.

In addition to above-mentioned components, the subject kits typically further include instructions for using the components of the kit to practice the subject methods, e.g., to prepare nucleic acid samples for perform the ROI amplicon process steps according to aspects of the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control samples and reagents, e.g., two or more control samples for use in testing the kit.

Utility

The ROI amplicon and normalization process described herein provides significant advantages in numerous applications. For example, the processes herein described allow one to analyze the sequence of multiple ROI's from multiple samples in a single sequencing reaction without losing low-copy number species (in the starting sample or amplified intermediates) as well as reducing the overrepresentation of high-copy number species. Thus, the ROI extraction and normalization processes described herein allow more efficient use of sequencing bandwidth, providing increased sequence coverage per run. In embodiments that employ multiplexed samples comprising polynucleotides coded with MID tags, sequences obtained can be correlated with their source sample (e.g., which individual has a specific sub-ROI sequence). This can be applied to a wide variety of applications, including identifying sequence variants and the individuals possessing such variants in a population and/or relating a specific sequence variation (or variations) to genetic predisposition to a phenotype in the population under study. Such populations occur in scientific research where the aim is to understand the link between phenotype and gene sequence as well as in clinical trials where one wishes to understand links between gene sequence of disease or between gene sequence and efficacy (or toxicity) of potential therapies and drug treatments. Similar applications of course exist in plants, animals, microorganisms and viruses, etc.

As currently practiced, extractions of ROI (e.g., as done using oligonucleotide probes on microarrays or in solution) generally rely on only one genomic region specific oligonucleotide sequence. In contrast, aspects of the present invention employ multiple independent sequence specific binding events at independent genomic locations. In many embodiments, ROI amplification/extraction uses three sequence specific primers. For example, the PCR reaction performed after circularization (an inverse PCR reaction) or after circularization followed by rolling circle amplification (standard PCR reaction) employs primers that bind to two different fragment-specific sites (sites c and b as shown in FIG. 3D). In addition, in certain embodiments, the PCR to produce the secondary ROI amplicons uses a primer specific for a third fragment specific site (e.g., site e as shown in FIG. 3E). Using these three independent sequence-specific binding events greatly increases the specificity of the ROI fragment enrichment/isolation process, thereby streamlining the subsequent analysis of these fragments (e.g., by reducing the number of fragments to be processed/sequenced).

Moreover, normalization by mixing (or 'blending') the individual ROI amplicons means that the representation of the individual sequence regions which comprise the ROI can be carefully controlled. This results in more uniform coverage of the different ROIs. If representations are significantly unequal, as can be the case in non-normalized samples, then one must have sufficient coverage for the least represented ROI. However, this results in gross over-representation of the more frequently occurring fragments, greatly increasing sequencing costs and/or time required for analysis. It is noted again, however, that a normalized sample does not necessarily contain substantially equal amounts (or numbers) of each ROI amplicon, as in certain embodiments a user may want different amounts of one or more ROI amplicon relative to other sub-ROI amplicons in the sample. No limitation in this regard is intended.

The ROI extraction/normalization processes described herein allow one to determine whether the ROI enriched polynucleotide sample being submitted to a sequencing process has a sufficient fragment representation, amount, and quality. This is in contrast to current approaches which require one to complete the entire workflow (including sequencing/analysis) to receive feedback on whether all the intermediate steps of the workflow are generating a sample of optimal quality. Thus, aspects of the subject invention provide a sample quality control step immediately prior to analysis (e.g., sequencing).

As noted above, aspects of the subject ROI extraction/normalization processes described herein are suited to the analysis of multiplexed samples, where the origin of each polynucleotide in the multiplexed sample can be determined based on the identity of an attached MID tag (or tags). In such aspects, the multiplexed polynucleotides are subjected to ROI amplification simultaneously. For example, a multiplex sample containing MID-tagged polynucleotides derived from 1,000 different individuals can be subjected to a single ROI enrichment reaction (e.g., in a single tube) followed by amplification of ten different sub-ROI in ten different reactions (e.g., in ten different tubes) which are then quantitated and mixed into a pooled normalized sample having known relative amounts of each multiplexed ROI.

This is in contrast to current amplification/normalization schemes in which the polynucleotides from each different individual (or source) are processed for ROI extraction and/or amplification independently. Processing 1,000 samples in this manner requires significantly more individual reactions to be performed as compared to the multiplex embodiments described above. For example, if 1,000 different individuals are to be assayed, for each ROI or sub-ROI of interest at least 1,000 different ROI extraction and amplification reactions would need to be performed followed by at least 1,000 different quantitation analyses prior to production of the normalized sample. This is a significantly more burdensome process than the multiplexed embodiments described herein.

It is further noted that the exemplary workflow described herein can be used to prepare polynucleotides for analysis by virtually any subsequent sequencing process, including both long-read processes (e.g, the Roche 454 sequencing platform) and short-read processes (e.g. the Illumina sequencing platform). The adapters can be specially designed to include the requisite domains (e.g., primer binding sites) used for each platform.

As described above, the subject invention is compatible with randomly fragmented libraries as well as sequence-specific fragmented libraries (e.g., those generated using restriction enzymes having sequence-specific cleavage sites). This flexibility means that 100% of the sequences in a polynucleotide sample (e.g., a genome) are theoretically accessible for ROI amplification and analysis.

The amplicon pools produced as described herein can be designed to have a defined amplicon size range, which enables library amplification, or immortalization, without the length biases observed in traditional restriction-fragmented libraries. It is noted here that the subject invention also is compatible with generating amplicon pools from restriction-fragmented polynucleotides/libraries.

In many embodiments of the present invention, circularization of the adapter-ligated fragments provides several advantages. First, the circularization process enables production of immortalized libraries, e.g., via rolling circle amplification. Second, circularization allows highly sequence specific amplification of ROI using PCR (e.g., inverse PCR), where the binding site for both primers is within the fragmented polynucleotides themselves, and not in the common adapter domains.

Finally, the present invention is amenable to being automated, thus enabling efficient ROI amplicon production and pooling from many hundreds, thousands or many thousands of individual samples (e.g., genomic DNA samples).

The above description is provided merely as exemplary of the utility of the subject invention, and is not in any way intended to limit the applicability of the invention to other mutation/variant identification endeavors.

EXAMPLES

Example I

Protocol Using FatI Digested DNA to Generate the Fragment Library Using a Restriction Enzyme for Fragmentation Adapter tagging. 4 µg genomic DNA (gDNA) was digested with 7 units of FatI (NEB) in a 100 µL reaction containing 1× NEBuffer 2 (50 mM NaCl, 10 mM Tris-HCl, 10 mM MgCl2, 1 mM Dithiothreitol, pH 7.9 @ 25° C.). The reaction was incubated at 55° C. for 2 hours, followed by heat inactivation at 65° C. for 20 min 50 µL of the FatI digested DNA was treated with 13 units Sequenase Version 2.0 DNA Polymerase (USB), in a reaction containing 1× fill in buffer (450 mM Tris pH8.0, 150 mM NaCl, 100 mM MgCl2, 60 mM Dithiothreitol) and 2.5 mM dCTP in a total volume of 100 µL. The reaction was incubated for 37° C. for 5 min, followed by heat inactivation at 75° C. for 20 min Adapters (see Table 2 below) were ligated in a 150 µL reaction containing 100 µL FatI digested-dCTP filled in DNA, 1× ligase buffer (84 mM Tris pH8.0, 46 mM Dithiothreitol), 0.5 mM ATP, 0.57 µM pre-annealed adapters (Table 2), and 2,400 units of T4 DNA ligase (NEB). The reaction was incubated at 16° C. for 1 hour 30 min before heat inactivation at 65° C. for 20 min.

Circularization. Adapter-tagged DNA was purified and concentrated using AMPure beads (Agencourt Bioscience) according to manufacturer's recommendations. 2.5 µg AMPure purified adapter-tagged DNA was circularized in a 50 µL reaction containing 1×Taq DNA ligase buffer (20 mM Tris-HCl, 25 mM potassium acetate, 10 mM Magnesium Acetate, 1 mM NAD, 10 mM Dithiothreitol, 0.1% Triton X-100, pH 7.6 @ 25° C.), 1.5 µM circularization oligonucleotide (Table 2) and 40 units of Taq DNA ligase (NEB). The reaction was incubated at 95° C. for 5 min followed by 45° C. for 90 min PCR amplification. 5 µL of circularized adapter-tagged DNA was used as template in a 50 µL reaction containing 0.3 µM each primer (one tailed with 454B titanium shotgun), 1× Colorless GoTaq Flexi Buffer (Promega), 2.5 mM $MgCl_2$, 0.2 mM each dNTP, and 1.25 Units GoTaq Hot Start Polymerase (Promega). 38 PCR reactions were performed targeting DCTD (5 sites), CDA (1 site), CYP1B1 (6 sites), CYP2C18 (3 sites), CYP2C8 (5 sites), CYP3A4 (7 sites), CYP3A5 (6 sites), NQO1 (2 sites) and UGT2B7 (3 sites). Cycling was 95° C. for 2 min followed by 31 cycles at 95° C. for 30 sec, 62° C. for 30 sec and 72° C. for 1 min and a final extension at 72° C. for 10 min Results. 38 FatI templates were targeted for PCR amplification, the templates having lengths between 227 bp and 1,407 bp. The predicted PCR products were estimated to be between 194 bp and 1157 bp.

After PCR amplification, amplicons were analyzed on a MultiNA Microchip Electrophoresis System (Shimadzu Biotech) (see FIG. 5). 94.74% (36/38) of the reactions generated amplicons. For the 36 positive amplicons there was a correlation between the predicted PCR product size and the MultiNA size estimate (R2=0.99). A single amplicon targeting CYP2C18 (1012 bp) was analyzed by 454 Titanium shotgun sequencing on ¹⁄₁₆th of a plate. 93.4% of sequencing reads that aligned to a unique human genomic location mapped to CYP2C18 (using the Burrows-Wheeler Aligner's Smith-Waterman Alignment and 1 kg v37 reference genome; http(colon)//www(dot) broadinstitute(dot)org/gsa/wiki/index.php/Downloading_the_GATK; see, Li H, Durbin R. Fast and accurate long-read alignment with Burrows-Wheeler transform. Bioinformatics. 2010 Mar. 1; 26(5):589-95).

TABLE 2

Oligonucleotide sequences for tagging and circularization of FatI digested DNA.

| NAME | SEQUENCE (5' to 3') | SEQ ID NO |
|---|---|---|
| Adapter oligo 1 | 5Phos/AGTGAGTCGCTCTGCTAC GTCTGAGTCGGAGACACGCAGGGA TGAGATGGCACATTCTA | 1 |
| Adapter oligo 2 | 5Phos/ATGTAGAATGTGTCTCCC TAT | 2 |
| Circularization oligo | CGACTCACTATAGGGAGA | 3 |

Example II

Randomly Fragmented DNA Protocol

Adapter tagging. gDNA was fragmented by Covaris AFA technology to a mean length of 1.6 kb and fragments were purified and concentrated using AMPure beads. 1,275 ng fragmented DNA was end-repaired firstly by SAP in a volume of 20 µL containing 1× FastAP reaction buffer, and 2.5 units FastAP (Fermentas). The reaction was incubated at 37° C. for 10 minutes, followed by 75° C. for 5 minutes. The 20 µL SAP reaction was further polished by addition of 0.4 mM dNTPs, 0.6 units T4 DNA polymerase (NEB) in a volume of 40 µl in a buffer consisting of 5 mM Tris.HCl pH 7.5, 7.5 mM MgCl2, and 1 mM DTT. The polishing reaction was incubated at 20° C. for 30 minutes followed by 75° C. for 20 minutes. Adapters were ligated by addition of 3990 units T4 DNA ligase (Enzymatics), with 30 µM annealed adapter (see Table 3) in a buffer consisting of 45 mM Tris.HCl pH 7.5, 5 mM MgCl2, and 9.5 mM DTT for 2 hours at 14° C., followed by 10 minutes at 65° C. The adapter ligated fragments were purified and concentrated using AMPure beads. Adapter ligated fragments were extended by addition of 1 µM extension primer (see Table 3), 200 µM each dNTP, and 0.5 µl Herculase II fusion polymerase (Stratagene) in 1× Herculase II buffer in a volume of 50 µL. The extension reaction was incubated at 95° C. for 5 minutes, 51° C. for 1 minute, followed by 72° C. for 10 minutes. The extension reaction was purified and concentrated using AMPure beads.

Phosphorylation and circularization. The extended adapter ligated fragments were phosphorylated by addition of 10 units T4 Polynucleotide kinase (NEB) in a volume of 45 µL in a 1×T4 DNA ligase buffer. The reaction was incubated at 37° C. for 30 minutes. Blunt ended phosphorylated fragments were circularized by addition of 5 µL (10,000 units) of T4 DNA ligase (NEB) and incubated at 16° C. for 90 minutes, followed by 65° C. for 10 minutes. The circularized library was treated with 5 µl ExoSAP (USB), 5 µL 5×GoTaq buffer (Promega), and 1 µL Exonuclease III (NEB) and incubated at 37° C. for 30 minutes, followed by 80° C. for 20 minutes.

Primary Inverse PCR. 5 targets were selected for enrichment. For each target a separate inverse PCR reaction was setup consisting of 200 µM each dNTP, 0.152 µM each forward and reverse primer, 2.5 mM MgCl2, 01.25 units GoTaq (Promega), and 3.15 µL circularized template in 1×GoTaq buffer in a volume of 50 µL. Cycling was 95° C. for 5 minutes followed by 35 cycles at 95° C. for 30 sec, 62° C. for 30 sec and 72° C. for 3 minutes, and a final extension at 72° C. for 10 minutes. PCR reactions were analyzed by gel electrophoresis and purified using AMPure beads.

Extension and secondary circularization. Purified PCR reactions were extended by addition of 1 µM extension primer (see Table 3), 200 µM each dNTP, and 0.5 µl Herculase II fusion polymerase (Stratagene) in 1× Herculase II buffer in a volume of 50 µL. The extension reaction was incubated at 95° C. for 5 minutes, 51° C. for 1 minute, followed by 72° C. for 10 minutes. Extension reactions were purified using AMPure beads. The purified extension reactions were circularized by addition of 1 µM splint oligonucleotide (see Table 3) in a final volume of 50 µL in 1×T4 DNA ligase buffer (NEB). Reactions were heated to 95° C. for 5 minutes, followed by 16° C. for 10 minutes before addition of 2.5 µL (2500 units) of T4 DNA ligase (NEB). Circularization reactions were incubated at 16° C. for 90 minutes followed by 65° C. for 10 minutes. Circularizations were treated with ExSAP (USB) and Exonuclease III in the same way as detailed above.

Secondary inverse PCR. PCR reactions were setup consisting of 200 µM each dNTP, 0.152 µM each primer (454A Titanium shotgun sequence, and final cleanup primer), 2.5 mM MgCl2, 1.25 units GoTaq (Promega), and 3.15 µL circularized template in 1×GoTaq buffer in a volume of 50 µL. Cycling was 95° C. for 5 minutes followed by 25 cycles at 95° C. for 30 sec, 62° C. for 30 sec and 72° C. for 3 minutes, and a final extension at 72° C. for 10 minutes.

Figure 6:
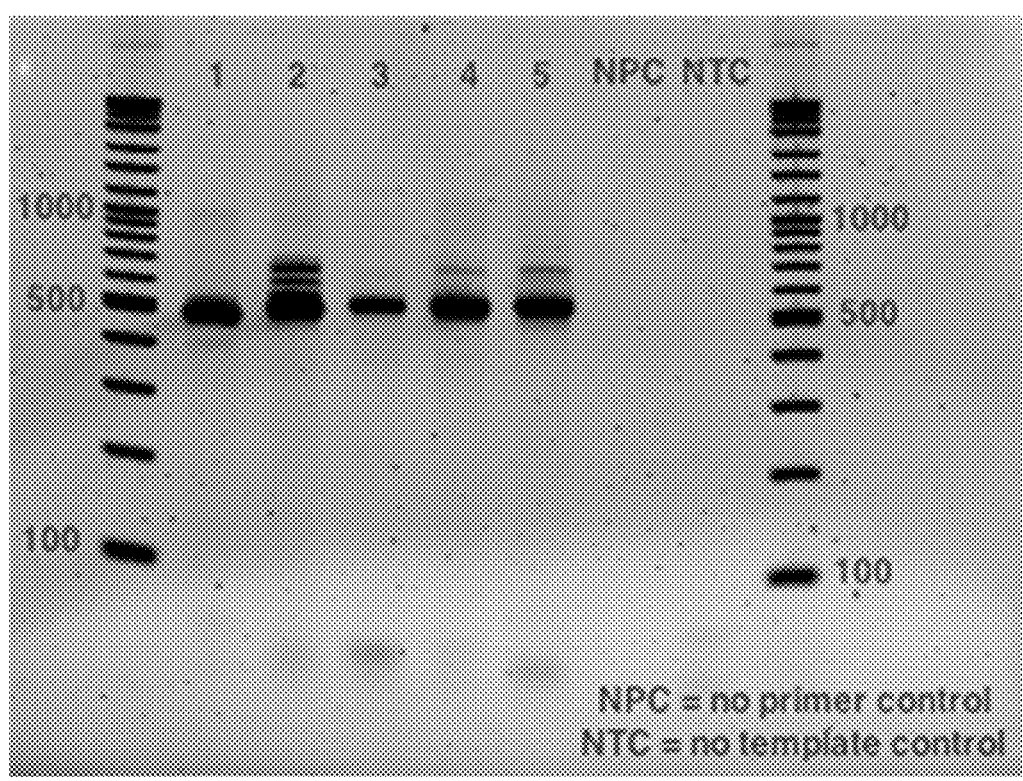
FIG. 6 shows electrophoretic analysis of secondary amplicons from 5 different regions of interest generated from randomly fragmented DNA (see Example II).

Results 5 µL of each reaction (1-5) were loaded on a 2% SYBR safe e-gel (Invitrogen) as shown in FIG. 6. Target sizes of 517 bp, 532 bp, 539 bp, 549 bp, and 553 bp are seen for regions 1-5 respectively. Confirmation of each target enrichment was achieved by dideoxy sequencing from 454A and 454B primers.

TABLE 3

Oligonucleotide sequences for tagging and circularization of randomly fragmented DNA

| NAME | SEQUENCE (5' to 3') | SEQ ID NO |
|---|---|---|
| Adapter oligo 1 | GACACGCAGGGATGAGATGG/3ddC | 4 |
| Adapter oligo 2 | 5Phos/GCCATCTCATCCCTGCGTGTCT CCGACTCAGTCTCCCTATAGTGAGTCG | 5 |
| Extension primer | 5Phos/CGACTCACTATAGGGAGA | 6 |
| Splint oligo | TCTCCCTATAGTGAGTCGTGCATCGCG | 7 |

Example III

Figure 7:
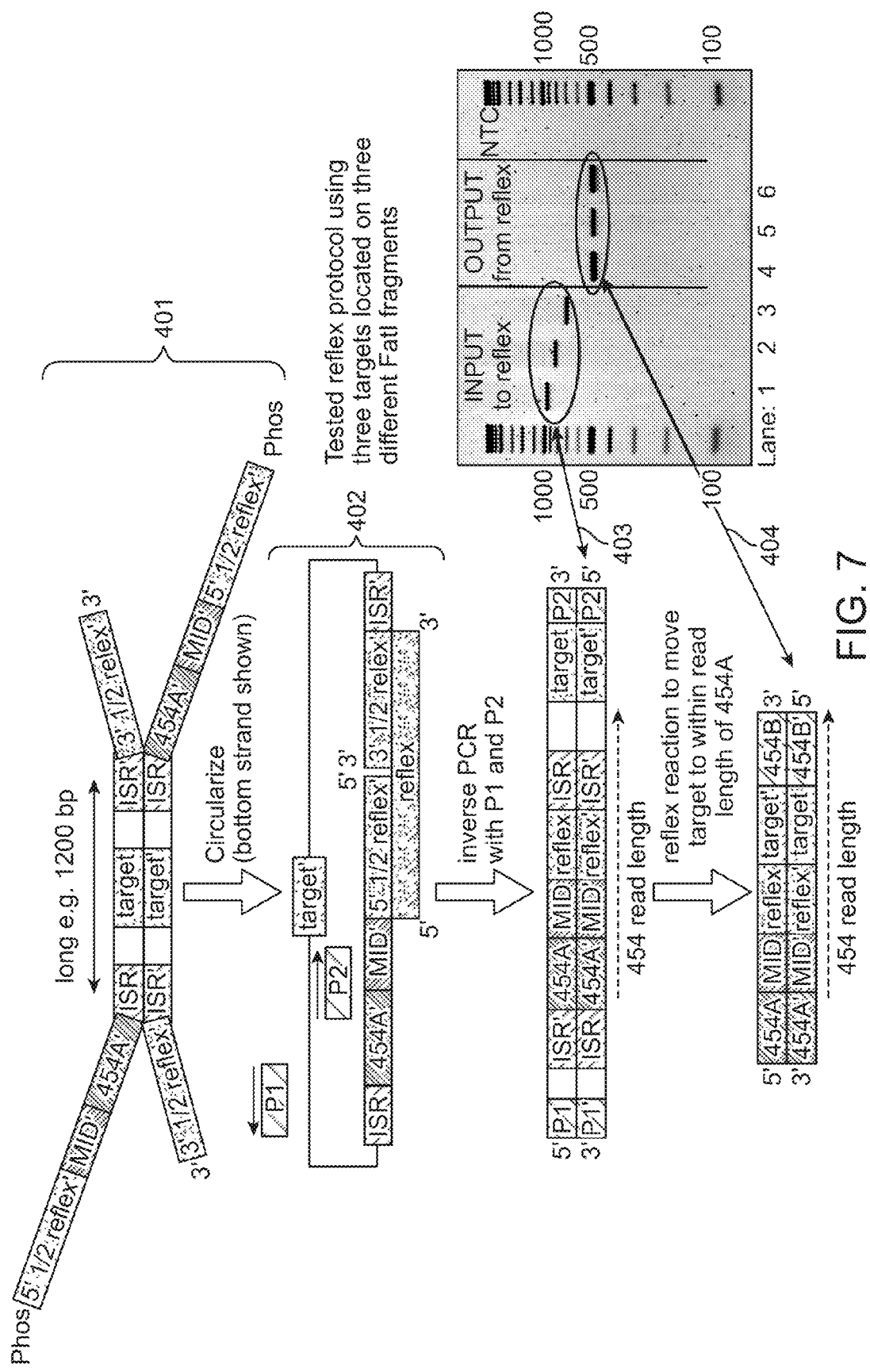
FIG. 7 shows the steps and resultant fragments produced in a reflex process performed on three targets located on three different FatI library fragments (see Example III).

Reflex Reaction of FatI Library to Generate Structurally Defined Secondary Amplicons FIG. 7 shows the workflow steps (left) and results (right) of an exemplary reflex reaction to generate structurally defined secondary ROI amplicons. The structure of the adapter employed is the same as shown in Table 2 in order to enable the reflex process to occur. Fragments 401 (generated in the FatI protocol described above) were circularized to produce circularized sample 402. The circularized population was then subjected to three inverse PCR reactions to produce specific amplification products 403 from the genes NQO1 (lane 1 on the gel on the right), CYP2C8 (lane 2 on the gel on the right) and CYP2C19 DMG (lane 3 on the gel on the right), each of which resides on a different FatI fragment. The relative location of the primers used in the inverse PCR reactions are shown as P1 and P2, with the direction of nucleic acid synthesis indicated by the arrow.

Each of these products was then subjected to a reflex process designed to place the target ROI within functional proximity to the 454A sequencing primer binding site, which generates structurally defined amplicons of ~500 bp in length (404). The reflex process was performed as follows. Inverse PCR products were diluted 1/1000 in dH₂0. 3 µl of the diluted PCR product was added to a 25 µl extension reaction consisting of 0.4 mM dNTPs, 1% DMSO, 0.5 µl EXL polymerase, and 1 µM reflex tailed primer in the appropriate 1× buffer for EXL DNA polymerase (Stratagene). Reactions were placed in a thermocycler and incubated at 92° C. for 5 minutes, 56° C. for 30 seconds, and 68° C. for 10 mins. Extension reactions were purified by AMPure beads into 17.75 µl dH₂0 and added to a reflex reaction in the same reaction conditions as the first extension, but with 454A primer instead of reflex primer. Reactions were placed in a thermocycler and incubated at 92° C. for 5 minutes and 30 seconds, 56° C. for 30 seconds, 68° C. for 10 minutes, 92° C. for 30 seconds, 51° C. for 5 minutes, 68° C. for 10 minutes, 92° C. for 30 seconds, 56° C. for 30 seconds, and 68° C. for 10 minutes. Reflex reactions were purified by AMPure and eluted in 40 µl dH₂0. Final PCR reactions were set up with 10 µl reflex reaction, 0.25 µM primers (454A, and internal primer for each fragment tailed with 454B), 0.2 mM dNTPs, 0.5 µl HotStarTaq (Qiagen) in a volume of 50 µl in the appropriate 1× buffer. PCR reactions were placed in a thermocycler and incubated at 95° C. for 15 minutes, followed by 30 cycles of 95° C. for 1 minute, 60° C. for 1 minute, 72° C. for 1 minute, before a final extension at 72° C. for 10 minutes. PCR reactions were analysed by gel electrophoresis.

As shown in lanes 4, 5, and 6 on the gel on the right (which correspond to the reflex products from the fragments shown in lanes 1, 2, and 3 respectively), the reflex process resulted in amplicons having the desired length (~500 bp) for each of the three different ROIs amplified. Sequencing of the reflex process-generated amplicons shown in lanes 4, 5, and 6 confirmed their identities and the relative positions of adapter domains and the ROI.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for amplifying a region of interest from multiple polynucleotide samples, comprising:

(a) combining asymmetrically tagged polynucleotides derived from multiple polynucleotide samples to generate a pooled library, wherein the asymmetrically tagged polynucleotides each comprise:

(i) a polynucleotide having a first end and second end;

(ii) a first adapter sequence on the first end of the polynucleotide comprising a secquence tag that identifies the source from which the polynucleotide is derived; and (iii) a second adapter sequence on the second end of the polynucleotide;

wherein the first adapter sequence and the second adapter sequence are not identical;

(b) circularizing the asymmetrically tagged polynucleotides in the pooled library intramolecularly to produce a circularized pooled library; and (c) performing an inverse polymerase chain reaction (iPCR) with an iPCR primer pair on the circularized pooled library to generate amplicons, wherein the iPCR primer pair targets the region of interest, and wherein each amplicon comprises:

(i) all or part of the region of interest;

(ii) the sequence tag; and (iii) all or part of the first adapter, all or part of the second adapter, or a combination thereof;

thereby amplifying a tagged region of interest from the multiple polynucleotide samples.

2. The method of claim 1, the method further comprising generating the asymmetrically tagged polynucleotides prior to the combining step, wherein generating the asymmetrically tagged polynucleotides comprises:

fragmenting polynucleotides in each of the multiple polynucleotide samples to produce fragmented polynucleotide samples; and attaching an asymmetric adapter to the polynucleotide fragments in each of the fragmented polynucleotide samples, wherein the asymmetric adapter comprises a first polynucleotide strand hybridized to a second polynucleotide strand, wherein the asymmetric adapter comprises an inner stem region (ISR) and an unpaired region, wherein the first polynucleotide strand comprises the first adapter sequence and the second polynucleotide strand comprises the second adapter sequence.

3. The method of claim 2, wherein the fragmenting is done in a sequence-specific manner.

4. The method of claim 2, wherein the fragmenting is done in a non sequence-specific manner.

5. The method of claim 4, further comprising size-selecting the pooled library prior to the circularizing step.

6. The method of claim 1, wherein the terminal sequences of first adapter and the second adapter generate a reflex sequence upon circularization.

7. The method of claim 6, wherein the performing step further comprises:
performing a reflex reaction on the amplicons to generate reflex products; and
performing a PCR reaction with a PCR primer pair on the reflex products to generate secondary amplicons, wherein the PCR primer pair targets the region of interest.

8. The method of claim 1, wherein the multiple polynucleotide samples are genomic DNA samples derived from different subjects.

9. The method of claim 1, further comprising size-selecting the amplicons generated in the performing step.

10. The method of claim 1, wherein the performing step further comprises:
circularizing the amplicons intramolecularly to generate a circularized amplicon sample; and
performing a PCR reaction with a PCR primer pair on the circularized amplicon sample to generate secondary amplicons, wherein the PCR primer pair targets the region of interest.

11. The method of claim 1, wherein the circularizing step employs a splint oligonucleotide comprising sequences complimentary to all or a portion of the terminal sequences of first adapter and the second adapter.

12. The method of claim 1, wherein the performing step comprises generating multiple different populations of amplicons with multiple different iPCR primer pairs each targeting a different region of interest, wherein each different population of amplicons comprises all or part of one of the different region of interest.

13. The method of claim 12, the method further comprising generating a pooled amplicon sample comprising the multiple different populations of amplicons.

14. The method of claim 13, wherein generating the pooled amplicon sample comprises:
quantitating each of the multiple different populations of amplicons; and
combining the multiple different populations of amplicons at known molar or mass ratios based on the quantitating to produce the pooled amplicon sample.

15. The method of claim 14, wherein each of the multiple different populations of amplicons has a polynucleotide length from 100 to 2000 bases.

16. A method for amplifying a region of interest from multiple polynucleotide samples, comprising:
(a) combining asymmetrically tagged polynucleotides derived from multiple polynucleotide samples to generate a pooled library, wherein the asymmetrically tagged polynucleotides each comprise:
(i) a polynucleotide having a first end and second end;
(ii) a first adapter sequence on the first end of the polynucleotide comprising a sequence tag that identifies the source from which the polynucleotide is derived; and
(iii) a second adapter sequence on the second end of the polynucleotide;
wherein the first adapter sequence and the second adapter sequence are not identical;
(b) circularizing the asymmetrically tagged polynucleotides in the pooled library intramolecularly to produce a circularized pooled library;
(c) generating linear concatameric polynucleotides from the circularized pooled library; and
(d) performing an inverse polymerase chain reaction (iPCR) with an iPCR primer pair on the linear concatameric polynucleotides from the circularized pooled library to generate amplicons, wherein the iPCR primer pair targets the region of interest, and wherein each amplicon comprises;
(i) all or part of the region of interest;
(ii) the sequence tag; and
(iii) all or part of the first adapter, all or part of the second adapter, or a
combination thereof;
thereby amplifying a tagged region of interest from the multiple polynucleotide samples.

17. The method of claim 16, wherein, prior to performing the inverse polymerase chain reaction, the linear concatameric polynucleotides from the circularized pooled library are fragmented.

18. The method of claim 16, wherein generating linear concatameric polynucleotides from the circularized pooled library comprises amplifying the circularized pooled library with a strand displacing polymerase.

* * * * *